US008768486B2

(12) United States Patent  
Gray et al.

(10) Patent No.: US 8,768,486 B2
(45) Date of Patent: Jul. 1, 2014

(54) MEDICAL LEADS WITH FREQUENCY INDEPENDENT MAGNETIC RESONANCE IMAGING PROTECTION

(75) Inventors: Robert W. Gray, Rochester, NY (US); Stuart G. MacDonald, Pultneyville, NY (US); Lon E. Smith, Jr., Rochester, NY (US)

(73) Assignee: Medtronic, Inc., Minneapolis, MN (US)

( * ) Notice: Subject to any disclaimer, the term of this patent is extended or adjusted under 35 U.S.C. 154(b) by 1896 days.

(21) Appl. No.: 11/953,443

(22) Filed: Dec. 10, 2007

(65) Prior Publication Data

US 2008/0147154 A1   Jun. 19, 2008

Related U.S. Application Data

(60) Provisional application No. 60/869,507, filed on Dec. 11, 2006.

(51) Int. Cl.
*A61N 1/00* (2006.01)
(52) U.S. Cl.
USPC ............................................. 607/115
(58) Field of Classification Search
USPC ............................................. 607/63, 115–122
See application file for complete search history.

(56) References Cited

U.S. PATENT DOCUMENTS

| | | | |
|---|---|---|---|
| 4,320,763 A | 3/1982 | Money | |
| 4,628,934 A * | 12/1986 | Pohndorf et al. | 607/27 |
| 4,661,530 A | 4/1987 | Gogolewski et al. | |
| 4,745,923 A * | 5/1988 | Winstrom | 607/9 |
| 4,830,003 A | 5/1989 | Wolff et al. | |
| 4,886,062 A | 12/1989 | Wiktor | |
| 5,133,732 A | 7/1992 | Wiktor | |
| 5,170,802 A | 12/1992 | Mehra | |
| 5,217,010 A * | 6/1993 | Tsitlik et al. | 607/9 |
| 5,304,200 A | 4/1994 | Spaulding | |
| 5,320,100 A | 6/1994 | Herweck et al. | |
| 5,336,253 A * | 8/1994 | Gordon et al. | 607/122 |
| 5,507,767 A | 4/1996 | Maeda et al. | |
| 5,630,829 A | 5/1997 | Lauterjung | |
| 5,649,965 A | 7/1997 | Pons et al. | |
| 5,702,419 A | 12/1997 | Berry et al. | |
| 5,725,572 A | 3/1998 | Lam et al. | |
| 5,727,552 A | 3/1998 | Ryan | |

(Continued)

FOREIGN PATENT DOCUMENTS

| | | |
|---|---|---|
| EP | 0 288 539 A1 | 7/1987 |
| WO | 03015662 A1 | 2/2003 |

OTHER PUBLICATIONS

International Search Report for International Application No. PCT/US2007/025366, mailed Jun. 24, 2008.

(Continued)

*Primary Examiner* — Christopher D Koharski
*Assistant Examiner* — Roland Dinga
(74) *Attorney, Agent, or Firm* — Michael J. Ostrom; Stephen W. Bauer

(57) ABSTRACT

A medical device having a frequency independent circuit that substantially reduces induced currents in a lead assembly and at a tissue interface. The frequency independent circuit configures an electrical path such that a stimulation pulse travels from the medical device to a selected tissue, and a current induced by an external changing electromagnetic signal is prevented from travelling the electrical path from the selected tissue to the medical device.

13 Claims, 25 Drawing Sheets

(56) References Cited

U.S. PATENT DOCUMENTS

| | | |
|---|---|---|
| 5,797,970 A * | 8/1998 | Pouvreau ........................... 607/9 |
| 5,824,045 A | 10/1998 | Alt |
| 5,860,999 A | 1/1999 | Schnepp-Pesch et al. |
| 5,931,867 A | 8/1999 | Haindl |
| 5,968,086 A * | 10/1999 | Bonner et al. ................ 607/122 |
| 6,032,063 A | 2/2000 | Hoar et al. |
| 6,033,436 A | 3/2000 | Steinke et al. |
| 6,074,362 A | 6/2000 | Jang et al. |
| 6,077,298 A | 6/2000 | Tu et al. |
| 6,083,258 A | 7/2000 | Yadav |
| 6,117,167 A | 9/2000 | Goicoechea et al. |
| 6,123,722 A | 9/2000 | Fogarty et al. |
| 6,156,064 A | 12/2000 | Chouinard |
| 6,159,239 A | 12/2000 | Greenhalgh |
| 6,168,619 B1 | 1/2001 | Dinh et al. |
| 6,183,508 B1 | 2/2001 | Stinson et al. |
| 6,183,509 B1 | 2/2001 | Dibie |
| 6,221,099 B1 | 4/2001 | Andersen et al. |
| 6,221,100 B1 | 4/2001 | Strecker |
| 6,221,102 B1 | 4/2001 | Baker et al. |
| 6,224,625 B1 | 5/2001 | Jayaraman |
| 6,228,111 B1 | 5/2001 | Törmälä et al. |
| 6,231,516 B1 | 5/2001 | Keilman et al. |
| 6,238,491 B1 | 5/2001 | Davidson et al. |
| 6,241,691 B1 | 6/2001 | Ferrera et al. |
| 6,251,136 B1 | 6/2001 | Guruwaiya et al. |
| 6,272,370 B1 | 8/2001 | Gillies et al. |
| 6,280,385 B1 | 8/2001 | Melzer et al. |
| 6,325,822 B1 | 12/2001 | Chouinard et al. |
| 6,350,279 B1 | 2/2002 | McGuinness |
| 6,393,314 B1 | 5/2002 | Watkins et al. |
| 6,424,234 B1 | 7/2002 | Stevenson |
| 6,451,026 B1 | 9/2002 | Biagtan et al. |
| 6,471,645 B1 | 10/2002 | Warkentin et al. |
| 6,496,006 B1 | 12/2002 | Vrijheid |
| 6,501,978 B2 | 12/2002 | Wagshul et al. |
| 6,503,272 B2 | 1/2003 | Duerig et al. |
| 6,506,972 B1 | 1/2003 | Wang |
| 6,564,084 B2 | 5/2003 | Allred, III et al. |
| 6,606,513 B2 | 8/2003 | Lardo et al. |
| 6,628,980 B2 | 9/2003 | Atalar et al. |
| 6,673,999 B1 | 1/2004 | Wang et al. |
| 6,675,049 B2 | 1/2004 | Thompson et al. |
| 6,700,472 B2 | 3/2004 | Wang et al. |
| 6,701,176 B1 | 3/2004 | Halperin et al. |
| 6,712,844 B2 | 3/2004 | Pacetti |
| 6,713,671 B1 | 3/2004 | Wang et al. |
| 6,714,809 B2 | 3/2004 | Lee et al. |
| 6,765,144 B1 | 7/2004 | Wang et al. |
| 6,767,360 B1 | 7/2004 | Alt et al. |
| 6,802,857 B1 | 10/2004 | Walsh et al. |
| 6,815,609 B1 | 11/2004 | Wang et al. |
| 6,822,548 B2 | 11/2004 | Wang et al. |
| 6,824,512 B2 | 11/2004 | Warkentin et al. |
| 6,829,509 B1 | 12/2004 | MacDonald et al. |
| 6,844,492 B1 | 1/2005 | Wang et al. |
| 6,846,985 B2 | 1/2005 | Wang et al. |
| 6,847,837 B1 | 1/2005 | Melzer et al. |
| 6,864,418 B2 | 3/2005 | Wang et al. |
| 6,876,886 B1 | 4/2005 | Wang |
| 6,898,454 B2 | 5/2005 | Atalar et al. |
| 6,906,256 B1 | 6/2005 | Wang |
| 7,048,716 B1 | 5/2006 | Kucharczyk et al. |
| 7,087,077 B1 | 8/2006 | Van Dijk et al. |
| 7,091,412 B2 | 8/2006 | Wang et al. |
| 7,304,277 B2 | 12/2007 | Weber |
| 2001/0044651 A1 | 11/2001 | Steinke et al. |
| 2002/0040185 A1 | 4/2002 | Atalar et al. |
| 2002/0107562 A1 | 8/2002 | Hart et al. |
| 2002/0111542 A1 | 8/2002 | Warkentin et al. |
| 2002/0128691 A1 | 9/2002 | Connelly |
| 2002/0138135 A1 | 9/2002 | Duerig et al. |
| 2002/0156515 A1 | 10/2002 | Jang et al. |
| 2002/0161402 A1 * | 10/2002 | Vogel et al. ...................... 607/1 |
| 2002/0161421 A1 | 10/2002 | Lee et al. |
| 2002/0188345 A1 | 12/2002 | Pacetti |
| 2003/0018369 A1 | 1/2003 | Thompson et al. |
| 2003/0036776 A1 | 2/2003 | Foster et al. |
| 2003/0050557 A1 * | 3/2003 | Susil et al. ..................... 600/424 |
| 2003/0088178 A1 | 5/2003 | Owens et al. |
| 2003/0105509 A1 | 6/2003 | Jang et al. |
| 2003/0120148 A1 | 6/2003 | Pacetti |
| 2003/0135114 A1 | 7/2003 | Pacetti et al. |
| 2003/0135268 A1 | 7/2003 | Desai |
| 2003/0171670 A1 | 9/2003 | Gumb et al. |
| 2003/0199768 A1 | 10/2003 | Cespedes et al. |
| 2003/0204217 A1 | 10/2003 | Greatbatch |
| 2004/0077995 A1 | 4/2004 | Ferek-Petric et al. |
| 2004/0078067 A1 | 4/2004 | Thompson et al. |
| 2004/0093075 A1 | 5/2004 | Kuehne |
| 2004/0138733 A1 | 7/2004 | Weber et al. |
| 2004/0143318 A1 | 7/2004 | Tseng et al. |
| 2004/0158310 A1 | 8/2004 | Weber et al. |
| 2004/0164836 A1 | 8/2004 | Wang et al. |
| 2004/0176822 A1 | 9/2004 | Thompson et al. |
| 2004/0181177 A1 | 9/2004 | Lee et al. |
| 2004/0210289 A1 | 10/2004 | Wang et al. |
| 2004/0225213 A1 | 11/2004 | Wang et al. |
| 2004/0249428 A1 | 12/2004 | Wang et al. |
| 2004/0249440 A1 | 12/2004 | Bucker et al. |
| 2004/0263172 A1 * | 12/2004 | Gray et al. ...................... 324/322 |
| 2004/0263173 A1 | 12/2004 | Gray |
| 2004/0263174 A1 | 12/2004 | Gray et al. |
| 2005/0004654 A1 | 1/2005 | Khosravi et al. |
| 2005/0033407 A1 | 2/2005 | Weber et al. |
| 2005/0043761 A1 | 2/2005 | Connelly et al. |
| 2005/0065437 A1 | 3/2005 | Weber et al. |
| 2005/0080346 A1 | 4/2005 | Gianchandani et al. |
| 2005/0155779 A1 | 7/2005 | Wang et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0283167 A1 | 12/2005 | Gray |
| 2006/0030774 A1 | 2/2006 | Gray et al. |
| 2006/0036311 A1 | 2/2006 | Nakayama et al. |
| 2006/0118319 A1 | 6/2006 | Wang et al. |
| 2006/0136039 A1 | 6/2006 | Martin |
| 2006/0142813 A1 | 6/2006 | Maschke |
| 2006/0282153 A1 | 12/2006 | Jang |
| 2007/0032862 A1 | 2/2007 | Weber et al. |
| 2007/0168016 A1 | 7/2007 | Gronemeyer et al. |
| 2007/0239256 A1 | 10/2007 | Weber et al. |
| 2008/0033497 A1 | 2/2008 | Bulkes et al. |
| 2008/0058913 A1 | 3/2008 | Gray et al. |
| 2010/0023095 A1 * | 1/2010 | Stevenson et al. ............... 607/63 |

OTHER PUBLICATIONS

Taal, et al., Potential Risks and Artifacts of Magnetic Resonance Imaging of Self-Expandable Esophageal Stents, Gastrointestinal Endoscopy, vol. 46, No. 5, 1997, at 424-429.

Tamai, M.D. et al., Initial and 6-Month Results of Biodegradable Poly-I-Lactic Acid Coronary Stents in Humans, Circulation, Jul. 25, 2000, at 399-404 http://www.circulationaha.org.

Tamai, M.D., et al., A Biodegradable Poly-I-Lactic Acid Coronary Stent in the Porcine Coronary Artery, Journal of Interventional Cardiology, vol. 12, No. 6, 1999 at 443-449.

Tsuji, MD, et al, Experimental and Clinical Studies of Biodegradable Polymeric Stents, Journal of Interventional Cardiology, vol. 13, Nov. 6, 2000, at 439-445.

Wendt,et al., Visualisation, Tracking and Navigation of Instruments for MN-Guided Interventional Procedures, Min Invas Ther & Allied Technol, vol. 8, No. 5, at 317-326.

Arno Buecker, et al., "Artifact-Free In-Stent Lumen Visualization by Standard Magnetic Resonance Angiography Using a New Metallic Magnetic Resonance Imaging Stent" Circulation, Apr. 16, 2002, pp. 1772-1775.

Lambertus W. Bartels et al., "MR Imaging of Vascular Stents: Effects of Susceptibility, Flow, and Radiofrequency Eddy Currents," pub-

(56) References Cited

OTHER PUBLICATIONS lished in Journal of Vascular and Interventional Radiology, vol. 12, No. 3, Mar. 2001, pp. 365-371.

Lambertus W. Bartels, et Al., "Improved Lumen Visualization in Metallic Vascular Implants by Reducing RF Artifacts," published in Magnetic Resonance in Medicine, 74:171-180 (2002).

Adam, M.D., et al., Interventional Magnetic Resonance Angiography, Seminars in Interventional Radiology, vol. 16, No. 1, 1991, at 31-37.

Amano, M.D., et al., Metallic Artifacts of Coronary and Iliac Arteries Stents in MRI Angiography and Contrast-Enhanced CT, Clinical Imaging, vol. 23, No. 2, Mar./Apr. 1999, at 85-89.

Bakker, et al., MR-Guided Balloon Angioplasty: In Vitro Demonstration of the Potential of MRI for Guiding Monitoring, and Evaluating Endovascular Interventions, JMRI, vol. 8, Jan./Feb. 1998, at 245-250.

CDRH Magnetic Resonance Working Group, A Primer on Medical Device Interactions With Magnetic Resonance Imaging Systems, http://www.fda/gov/cdrh/ode/ primerf6.html, Mar. 5, 2000, at 1-18.

Colombo, M.D., et al., Biodegradable Stents "Fulfilling TheMission and Stepping Away" Circulation 2000, Jul. 25, 2000, 202:371-373 http://www.circulationaha.org.

De Cobelli, et al., MRI Assessment of Coronary Stents Valutazione RMDelgi Stent Coronarici,RAYS, vol. 24, No. 1, 1999 at 140-148.

Duerinckx, M.D., et al., Assessment of Coronary Artery Patency After Stent Placement Using Magnetic Resonance Angiography, JMRI, vol. 8, No. 4, Jul./Aug. 1998, at 896-902.

Friedrich, et al., Behavior of Implantable Coronary Stents During Magnetic Resonance Imaging, International Journal of Cardiovascular Interventions, vol. 2, at 217-222, Nov. 1999.

Girard, et al., Wallstent Metallic Biliary Endoprothesis: MR Imaging Characteristics, Radiology, vol. 184, No. 3, at 874-876, Sep. 1992.

Hilfiker, M.D, et al., Plain and Covered Stent-Grafts: In Vitro Evaluation of Characteristics At Three Dimensional MR Angiography, Radiology, vol. 211, No. 3, Jun. 1999, at 693-697.

Hug, M.D. et al., Cornary Arterial Stents: Safety and Arifacts During MRI Imagining, Radiology 2000, vol. 216, Nov. 3, at 781-787.

Kee, M.D., et al, MR-Guided Transjugular Portosystemic Shunt Placement in a Swine Model,JVIR, vol. 10, No. 5, May 1999, at 529-535.

Laissy, et al., Magnetic Resonance Angiography of Intravascular Endoprotheses: Investigation of Three Devices, Cardiovascular and Interventional Radiology, vol. 18, 1995, at 360-366.

Lardo, Ph.D., Real-Time Magnetic Resonance Imagining: Diagnostic and Interventional Applications, Pediatric Cardiology vol. 21, 2000, at 80-98.

Lenhart, M.D., et al., Stent Appearance at Contrast-Enhanced MR Angiography: In Vitro Examination with 14 Stents, Radiology Oct. 2000, vol. 271, No. 1, at 173-178.

Lufkin, et al., Interventional MRI: Update, European Radiology, vol. 7, (Suppl. 5), 1997 at 187-200.

Manke,C.; Stentagioplastie von Beckenarterienstenosen unter MRI-Kontrolle: Erste klinische Ergebnisse, Fotschr Rontgenstr, 2000:172, at 92-97.

Manke, MD, et al.; Magnetic Resonance Monitoring of Stent Deployment In Vitro Evaluation of Different Stent Designs and Stent Delivery Systems, Investigative Radiology, vol. 35, No. 6, Jun. 2000, at 343-351.

Matsumoto,et al.; Gadolinium Enhanced MR Imagining of Vascular Stents, Journal of Computer Assisted Tomography, vol. 14, No. 3, May/Jun. 1990, at 357-361.

Matsumoto, et al., Tantalum Vascular Stents: In Vivo Evaluation With MR Imagining, Radiology, vol. 170, No. 3, Mar. 1989, at 753-755.

Nitatori, et al., MRI Artifacts of Metallic Stents Derived From Imaging Sequencing and the Ferromagnetic Nature of Materials, Radiation Medicine, vol. 17, No. 4, 1999, at 329-334.

Omary, M.D. et al, MR-Guided Angioplasty of Renal Artery Stenosis in a Pig Model: A Feasibility Study, J. JVIR 2000; vol. 11, at 373-381.

Schenck, The Role of Magnetic Susceptibility in MagneticResonance Imaging: MRI Magnetic Compatibility of the First and Second Kinds, Medical Physics, vol. 23, No. 6, Jun. 1996, at 815-850.

Shellock, Metallic Stents: Evaluation of MR Imaging Safety, AIR, vol. 173, Sep. 1999, at 543-547.

Strohm, et al., safety of Implantable Coronary Stents During 1 H-Magnetic Resonance Imaging at 1.0 and 1.5 T, Journal of Cardiovascular Magnetic Resonance vol. I, No. 3, 1999, at 239-245.

Stroman, et al., Will It Be Feasible to Insert Endoprostheses Under Interventional MRI?, J Endovasc-Surg, vol. 3, 1996, at 396-404.

\* cited by examiner

MEDICAL LEADS WITH FREQUENCY INDEPENDENT MAGNETIC RESONANCE IMAGING PROTECTION

CROSS-REFERENCE TO RELATED APPLICATION

This application claims the benefit of U.S. Provisional Patent Application No. 60/869,507 filed Dec. 11, 2006.

FIELD OF THE PRESENT INVENTION

The present invention is directed to a device for protecting a patient, physician, and/or electronic components in an electrical device implanted or partially implanted within the patient. More particularly, the present invention is directed to a device for protecting the conductive parts of the electrical device from current and voltage surges induced by magnetic resonance imaging systems' oscillating magnetic fields.

BACKGROUND OF THE PRESENT INVENTION

Magnetic resonance imaging has been developed as an imaging technique adapted to obtain both images of anatomical features of human patients as well as some aspects of the functional activities and characteristics of biological tissue. These images have medical diagnostic value in determining the state of the health of the tissue examined. Unlike the situation with fluoroscopic imaging, a patient undergoing magnetic resonance imaging procedure may remain in the active imaging system for a significant amount of time, e.g. a half-hour or more, without suffering any adverse effects.

In a magnetic-resonance imaging process, a patient is typically aligned to place the portion of the patient's anatomy to be examined in the imaging volume of the magnetic-resonance imaging apparatus. Such an magnetic resonance imaging apparatus typically comprises a primary electromagnet for supplying a constant magnetic field (B0) which, by convention, is along the z-axis and is substantially homogeneous over the imaging volume and secondary electromagnets that can provide linear magnetic field gradients along each of three principal Cartesian axes in space (generally x, y, and z, or x1, x2 and x3, respectively). The magnetic-resonance imaging apparatus also comprises one or more RF (radio frequency) coils that provide excitation and detection of the magnetic-resonance imaging induced signals in the patient's body.

The gradient fields are switched ON and OFF at different rates depending on the magnetic-resonance imaging scan sequence used. In some cases, this may result in a changing magnetic field on the order of dB/dt=50 T/s. The frequency that a gradient field may be turned ON can be between 200 Hz to about 300 kHz.

For a single loop with a fixed area, Lenz's law can be stated as:

$$EMF = -A @ dB/dt$$

where A is the area vector, B is the magnetic field vector, and "1" is the vector scalar product. This equation indicates that an electro-motive-force (EMF) is developed in any loop that encircles a changing magnetic field.

In a magnetic-resonance imaging system, there is applied to the biological sample (patient) a switched gradient field in all 3 coordinate directions (x-, y-, z-directions). If the patient has an implanted heart pacemaker (or other implanted devices having conductive components) the switched gradient magnetic fields (an alternating magnetic field) may cause:

1. Erroneous signals to be induced/generated in a sensing lead or device or circuit;
2. Damage to electronics; and/or
3. Harmful stimulation of tissue, e.g. heart muscle, nerves, etc.

As noted above, the use of the magnetic-resonance imaging process with patients who have implanted medical assist devices; such as cardiac assist devices or implanted insulin pumps; often presents problems. As is known to those skilled in the art, implantable devices (such as implantable pulse generators (IPGs) and cardioverter/defibrillator/pacemakers (CDPs)) are sensitive to a variety of forms of electromagnetic interference (EMI) because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging (magnetic-resonance imaging) procedure. Thus, patients with implantable devices are generally advised not to undergo magnetic resonance imaging (magnetic-resonance imaging) procedures.

To more appreciate the problem, the use of implantable cardiac assist devices during a magnetic-resonance imaging process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 Volts) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Moreover, problems are realized when the placement of the implant is next to particular organs. For example, when a pacemaker is placed in the upper chest and the lead tip is placed into the heart, a loop (an electrical loop) is created. A changing magnetic field (the switched gradient field) over the area of the loop (through the area of the loop) will cause an induced voltage (and current) across the heart. This induced voltage (current) can stimulate the heart inappropriately and can cause heart damage or death.

Therefore, it is desirable to provide a medical device or system that reduces or eliminates the undesirable effects of changing magnetic fields from a magnetic-resonance imaging system on the medical devices and/or patients undergoing medical procedures or that have temporary or permanent implanted materials and/or devices with conducting components.

SUMMARY OF THE PRESENT INVENTION

A first aspect of the present invention is a voltage compensation unit for reducing the effects of induced voltages upon a device to a safe level. The voltage compensation unit includes a sensing circuit to sense voltages induced in conductive components of the device, the voltages being induced by changing magnetic fields and a compensation circuit, operatively connected to the sensing circuit and responsive thereto, to provide opposing voltages to the device to reduce the effects of induced voltages caused by changing magnetic fields.

A second aspect of the present invention is a voltage compensation unit for reducing the effects of induced voltages upon a tissue invasive medical tool to a safe level. The voltage compensation unit includes a sensing circuit to sense voltages induced in conductive components of the medical tool, the voltages being induced by changing magnetic fields; a compensation circuit, operatively connected to the sensing circuit and responsive thereto, to provide opposing voltages to the medical tool to reduce the effects of induced voltages caused by changing magnetic fields; and a connection device to provide an electrical connection between the sensing circuit and the compensation circuit and the medical tool.

A third aspect of the present invention is a voltage compensation unit for reducing the effects of induced voltages upon a device to a safe level. The voltage compensation unit includes a communication circuit, communicatively linked to a magnetic-resonance imaging system, to receive information associated with a start and end of an application of changing magnetic fields produced by the magnetic-resonance imaging system and a compensation circuit, operatively connected to the communication circuit and responsive thereto, to synchronize application of opposing voltages to the device with the sensed changing magnetic fields, the opposing voltages reducing the effects of induced voltages caused by the changing magnetic fields.

A fourth aspect of the present invention is a voltage compensation unit for reducing the effects of induced voltages upon a device to a safe level. The voltage compensation unit includes a communication circuit, communicatively linked to a magnetic-resonance imaging system, to receive information associated with a start and end of an application of changing magnetic fields produced by the magnetic-resonance imaging system and a compensation circuit, operatively connected to the communication circuit and responsive thereto, to apply opposing voltages to the device, the opposing voltages reducing the effects of induced voltages caused by the changing magnetic fields.

A fifth aspect of the present invention is a voltage compensation unit for reducing the effects of induced voltages upon a device having a single wire line, the single wire line having a balanced characteristic impedance. The voltage compensation unit includes a tunable compensation circuit, operatively connected to the wire line, to apply supplemental impedance to the wire line, the supplemental impedance causing the characteristic impedance of the wire line to become unbalanced, thereby reducing the effects of induced voltages caused by changing magnetic fields.

Another aspect of the present invention is an electrical lead component for a medical device which reduces the effects of magnetic-resonance imaging induced signals. The electrical lead component includes a medical device electrical lead capable of providing an electrical path to a desired tissue region and a coil that generates a voltage due to a changing magnetic-resonance imaging electromagnetic field opposite to that which would be induced by the changing magnetic-resonance imaging electromagnetic field in the medical device electrical lead so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region and a plurality of coils, each coil generating a voltage due to a changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the medical device electrical lead so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region and three orthogonally planar coils, each coil generating a voltage due to a changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the medical device electrical lead so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region; a plurality of coils, each coil generating a voltage due to a changing magnetic resonance imaging electromagnetic field; a sensor to measure a strength of voltages induced by the changing magnetic-resonance imaging electromagnetic field; and a switching device, operatively connected to the sensor and plurality of coils, to operatively connect a number of the plurality of coils in response to the measured strength of voltages induced by the changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the medical device electrical lead so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region; three orthogonally planar coils, each coil generating a voltage due to a changing magnetic-resonance imaging electromagnetic field; a sensor to measure a strength of voltages induced by the changing magnetic-resonance imaging electromagnetic field; and a switching device, operatively connected to the sensor and the coils, to operatively connect a number of the coils in response to the measured strength of voltages induced by the changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the medical device electrical lead so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region; a plurality of coils, each coil generating a voltage due to a changing magnetic resonance imaging electromagnetic field; a transceiver to receive a signal indicating a number of coils to be connected; and a switching device, operatively connected to the transceiver and plurality of coils, to operatively connect a number of the plurality of coils in response to the received signal indicating the number of coils to be connected such that a combination of voltages due to a changing magnetic-resonance imaging electromagnetic field provides a combined voltage that is opposite to the voltage which would be induced by the changing magnetic-resonance imaging electromagnetic field in the medical device electrical lead so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region; three orthogonally planar coils, each coil generating a voltage due to a changing magnetic-resonance imaging electromagnetic field; a transceiver to receive a signal indicating a number of coils to be connected; and a switching device, operatively connected to the transceiver and the coils, to operatively connect a number of the coils in response to the received signal indicating the number of coils to be connected such that a combination of voltages due to a changing magnetic-resonance imaging electromagnetic field provides a combined voltage that is opposite to the voltage which would be induced by the changing magnetic resonance imaging electromagnetic field in the medical device electrical lead so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region and a coil that generates a voltage induced by a changing magnetic-resonance imaging electromagnetic field opposite to a voltage which would be induced by the changing magnetic resonance imaging electromagnetic field in the medical device so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region and a plurality of coils, each coil generating a voltage due to a changing magnetic-resonance imaging electromagnetic field such that a combination of voltages due to a changing magnetic-resonance imaging electromagnetic field provides a combined voltage that is opposite to the voltage which would be induced by the changing magnetic resonance imaging electromagnetic field in the medical device so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region and three orthogonally planar coils, each coil generating a voltage due to a changing magnetic resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the medical device so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region; a plurality of coils, each coil generating a voltage due to a changing magnetic-resonance imaging electromagnetic field; a sensor to measure a strength of voltages induced by the changing magnetic-resonance imaging electromagnetic field; and a switching device, operatively connected to the sensor and plurality of coils, to operatively connect a number of the plurality of coils in response to the measured strength of voltages induced by the changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the medical device so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region; three orthogonally planar coil, each coil generating a voltage due to a changing magnetic-resonance imaging electromagnetic field; a sensor to measure a strength of voltages induced by the changing magnetic-resonance imaging electromagnetic field; and a switching device, operatively connected to the sensor and plurality of coils, to operatively connect a number of the plurality of coils in response to the measured strength of voltages induced by changing magnetic-resonance imaging electromagnetic field such that a combination of voltages due to a changing magnetic-resonance imaging electromagnetic field provides a combined voltage that is opposite to the voltage which would be induced by the changing magnetic resonance imaging electromagnetic field in the medical device so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region; a plurality of coils, each coil generating a voltage due to a changing magnetic-resonance imaging electromagnetic field; a transceiver to receive a signal indicating a number of coils to be connected; and a switching device, operatively connected to the transceiver and the coils, to operatively connect a number of the coils in response to the received signal indicating the number of coils to be connected such that a combination of voltages due to a changing magnetic-resonance imaging electromagnetic field provides a combined voltage that is opposite to the voltage which would be induced by the changing magnetic-resonance imaging electromagnetic field in the medical device so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region; three orthogonally planar coil, each coil generating a voltage due to a changing magnetic-resonance imaging electromagnetic field; a transceiver to receive a signal indicating a number of coils to be connected; and a switching device, operatively connected to the transceiver and the coils, to operatively connect a number of the coils in response to the received signal indicating the number of coils to be connected such that a combination of voltages due to a changing magnetic-resonance imaging electromagnetic field provides a combined voltage that is opposite to the voltage which would be induced by the changing magnetic-resonance imaging electromagnetic field in the medical device so as to reduce voltages induced by the changing magnetic-resonance imaging electromagnetic field.

Another aspect of the present invention is an electrical lead component for a medical device which reduces the effects of magnetic-resonance imaging induced signals. The electrical lead component includes a medical device electrical lead capable of providing an electrical path to a desired tissue region; a voltage source; a sensor to sense voltages induced by the changing magnetic resonance imaging electromagnetic field; and a switching device, operatively connected to the sensor and voltage source, to operatively connect the voltage source to the medical device electrical lead in response to the sensed voltage induced by the changing magnetic-resonance imaging electromagnetic field such that the voltage source provides a voltage that is opposite to the voltage which would be induced by the changing magnetic-resonance imaging electromagnetic field in the medical device electrical lead so as to reduce voltages induced by the changing magnetic-resonance imaging electromagnetic field.

Another aspect of the present invention is a medical device for a medical device which reduces the effects of magnetic-resonance imaging induced signals. The medical device includes a medical device capable of providing medical treatment to a desired tissue region; a voltage source; a sensor to sense voltages induced by the changing magnetic-resonance imaging electromagnetic field; and a switching device, operatively connected to the sensor and voltage source, to operatively connect the voltage source to the medical device in response to the sensed voltage induced by the changing magnetic-resonance imaging electromagnetic field such that the voltage source provides a voltage that is opposite to the voltage which would be induced by the changing magnetic-resonance imaging electromagnetic field in the medical device so as to reduce voltages induced by the changing magnetic-resonance imaging electromagnetic field.

Another aspect of the present invention is a lead for medical applications that reduces the effects of magnetic-resonance imaging induced signals. The lead includes two coiled conductive strands forming a spring-like configuration such that current flows over a surface thereof, through contact points between adjacent loops of the coiled conductive strands and an insulating coating formed over a portion of the two coiled conductive strands such that an inline inductive element is formed, the current flowing along a curvature of the two coiled conductive strands in the insulating coated portion of the two coiled conductive strands.

Another aspect of the present invention is a lead for medical applications that reduces the effects of magnetic-resonance imaging induced signals. The lead includes two coiled conductive strands forming a spring-like configuration such that current flows over a surface thereof, through contact points between adjacent loops of the coiled conductive strands and an adjustable resistive material formed over a portion of the two coiled conductive strands such that an inline inductive element is formed, the current flowing along a curvature of the two coiled conductive strands in the adjustable resistive material portion of the two coiled conductive strands.

Another aspect of the present invention is a lead for medical applications that reduces the effects of magnetic-resonance imaging induced signals. The lead includes a coiled conductive strand forming a spring-like configuration such that current flows over a surface thereof, through contact points between adjacent loops of the coiled conductive strand and an insulating coating formed over a portion of the coiled conductive strand such that an inline inductive element is formed, the current flowing along a curvature of the coiled conductive strand in the insulating coated portion of the coiled conductive strand.

Another aspect of the present invention is a lead for medical applications that reduces the effects of magnetic-resonance imaging induced signals. The lead includes a coiled conductive strand forming a spring-like configuration such that current flows over a surface thereof, through contact points between adjacent loops of the coiled conductive strand and an adjustable resistive material formed over a portion of the coiled conductive strand such that an inline inductive element is formed, the current flowing along a curvature of the coiled conductive strand in the adjustable resistive material portion of the coiled conductive strand.

Another aspect of the present invention is a lead for medical applications that reduces the effects of magnetic-resonance imaging induced signals. The lead includes two coiled conductive strands forming a spring-like configuration such that current flows over a surface thereof, through contact points between adjacent loops of the coiled conductive strands; a first insulating coating formed over a first portion of the two coiled conductive strands such that a first inline inductive element having a first inductance is formed, the current flowing along a curvature of the two coiled conductive strands in the first insulating coated portion of two coiled conductive strands; and a second insulating coating formed over a second portion of the two coiled conductive strands such that a second inline inductive element having a second inductance is formed, the current flowing along a curvature of the two coiled conductive strands in the second insulating coated portion of two coiled conductive strands. The first inductance is different from the second inductance.

Another aspect of the present invention is a lead for medical applications that reduces the effects of magnetic-resonance imaging induced signals. The lead includes two coiled conductive strands forming a spring-like configuration such that current flows over a surface thereof, through contact points between adjacent loops of the coiled conductive strands; a first adjustable resistive material formed over a first portion of the two coiled conductive strands such that a first inline inductive element having a first inductance is formed, the current flowing along a curvature of the two coiled conductive strands in the first adjustable resistive material portion of the two coiled conductive strands; and a second adjustable resistive material formed over a second portion of the two coiled conductive strands such that a second inline inductive element having a second inductance is formed, the current flowing along a curvature of the two coiled conductive strands in the second adjustable resistive material portion of the two coiled conductive strands. The first inductance is different from the second inductance.

Another aspect of the present invention is a lead for medical applications that reduces the effects of magnetic-resonance imaging induced signals. The lead includes a coiled conductive strand forming a spring-like configuration such that current flows over a surface thereof, through contact points between adjacent loops of the coiled conductive strand; a first insulating coating formed over a first portion of the coiled conductive strand such that a first inline inductive element having a first inductance is formed, the current flowing along a curvature of the coiled conductive strand in the first insulating coated portion of the coiled conductive strand; and a second insulating coating formed over a second portion of the coiled conductive strand such that a second inline inductive element having a second inductance is formed, the current flowing along a curvature of the coiled conductive strand in the second insulating coated portion of the coiled conductive strand. The first inductance is different from the second inductance.

Another aspect of the present invention is a lead for medical applications that reduces the effects of magnetic-resonance imaging induced signals. The lead includes a coiled conductive strand forming a spring-like configuration such that current flows over a surface thereof, through contact points between adjacent loops of the coiled conductive strand; a first adjustable resistive material formed over a first portion of the coiled conductive strand such that a first inline inductive element having a first inductance is formed, the current flowing along a curvature of the coiled conductive strand in the first adjustable resistive material portion of the coiled conductive strand; and a second adjustable resistive material formed over a second portion of the coiled conductive strand such that a second inline inductive element having a second inductance is formed, the current flowing along a curvature of the coiled conductive strand in the second adjustable resistive material portion of the coiled conductive strand. The first inductance is different from the second inductance.

Another aspect of the present invention is an electrical lead for a medical device, the electrical lead capable of providing an electrical path to a desired tissue region, including a coil that generates a voltage due to a changing magnetic-resonance imaging electromagnetic field opposite to that which would be induced by the changing magnetic-resonance imaging electromagnetic field in the electrical lead without the coil so as to reduce voltages induced by the changing magnetic-resonance imaging electromagnetic field.

Another aspect of the present invention is an electrical lead for a medical device, the electrical lead capable of providing an electrical path to a desired tissue region, including a plurality of coils, at least one coil generating a voltage due to a changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the electrical lead without the plurality of coils so as to reduce voltages induced by the changing magnetic-resonance imaging electromagnetic field.

Another aspect of the present invention is an electrical lead for a medical device, the electrical lead capable of providing an electrical path to a desired tissue region, including planar coils, at least one coil generating a voltage due to a changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the electrical lead without the planar coils so as to reduce voltages induced by the changing magnetic-resonance imaging electromagnetic field.

Another aspect of the present invention is an electrical lead for a medical device, the electrical lead capable of providing an electrical path to a desired tissue region, including a plurality of coils, at least one coil generating a voltage due to a changing magnetic-resonance imaging electromagnetic field; a sensor to measure a strength of voltages induced by the changing magnetic resonance imaging electromagnetic field; and a switching device, operatively connected to the sensor and plurality of coils, to operatively connect a number of the plurality of coils in response to the measured strength of voltages induced by the changing magnetic-resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the electrical lead without the coils so as to reduce voltages induced by the changing magnetic-resonance imaging electromagnetic field.

Another aspect of the present invention is an electrical lead for a medical device, the electrical lead capable of providing an electrical path to a desired tissue region, including planar coils, at least one coil generating a voltage due to a changing magnetic-resonance imaging electromagnetic field; a sensor to measure a strength of voltages induced by the changing magnetic-resonance imaging electromagnetic field; and a switching device, operatively connected to the sensor and the coils, to operatively connect a number of the coils in response to the measured strength of voltages induced by the changing magnetic resonance imaging electromagnetic field such that a combination of voltages due to a changing magnetic-resonance imaging electromagnetic field provides a combined voltage that is opposite to the voltage which would be induced by the changing magnetic-resonance imaging electromagnetic field in the electrical lead without the planar coils so as to reduce voltages induced by the changing magnetic-resonance imaging electromagnetic field.

Another aspect of the present invention is an electrical lead for a medical device, the electrical lead capable of providing an electrical path to a desired tissue region, including a plurality of coils, at least one coil generating a voltage due to a changing magnetic-resonance imaging electromagnetic field; a transceiver to receive a signal indicating a number of coils to be connected; and a switching device, operatively connected to the transceiver and plurality of coils, to operatively connect a number of the plurality of coils in response to the received signal indicating the number of coils to be connected such that a combination of voltages due to a changing magnetic-resonance imaging electromagnetic field provides a combined voltage that is opposite to the voltage which would be induced by the changing magnetic-resonance imaging electromagnetic field in the electrical lead without the coils so as to reduce voltages induced by the changing magnetic-resonance imaging electromagnetic field.

Another aspect of the present invention is an electrical lead for a medical device, the electrical lead capable of providing an electrical path to a desired tissue region, including planar coils, at least one coil generating a voltage due to a changing magnetic-resonance imaging electromagnetic field; a transceiver to receive a signal indicating a number of coils to be connected; and a switching device, operatively connected to the transceiver and the coils, to operatively connect a number of the coils in response to the received signal indicating the number of coils to be connected such that a combination of voltages due to a changing magnetic-resonance imaging electromagnetic field provides a combined voltage that is opposite to the voltage which would be induced by the changing magnetic-resonance imaging electromagnetic field in the medical device electrical lead without the planar coils so as to reduce voltages induced by the changing magnetic-resonance imaging electromagnetic field.

Another aspect of the present invention is an electrical lead including an electrical strand to provide an electrical path between a tissue region and a medical device and a RF choke, operatively connected to the electrical strand, to significantly reduce currents induced by a changing magnetic resonance imaging electromagnetic field in the electrical strand. The RF choke allows a signal corresponding to a measured characteristic of the tissue region to pass therethrough.

Another aspect of the present invention is an electrical lead including an electrical strand to provide an electrical path between a tissue region and a medical device and a RF filter, operatively connected to the electrical strand, to significantly reduce currents induced by a changing magnetic resonance imaging electromagnetic field in the electrical strand. The RF filter allows a signal corresponding to a measured characteristic of the tissue region to pass therethrough.

Another aspect of the present invention is an electrical lead including an electrical strand to provide an electrical path between a tissue region and a medical device and a notch filter, operatively connected to the electrical strand, to significantly reduce currents induced by a changing magnetic resonance imaging electromagnetic field in the electrical strand. The notch filter allows a signal corresponding to a measured characteristic of the tissue region to pass therethrough.

Another aspect of the present invention is an electrical lead including an electrical strand to provide an electrical path between a tissue region and a medical device and a bandpass filter, operatively connected to the electrical strand, to significantly reduce currents induced by a changing magnetic resonance imaging electromagnetic field in the electrical strand. The band pass filter allows a signal corresponding to a measured characteristic of the tissue region to pass therethrough.

Another aspect of the present invention is an electrical lead including an electrical strand to provide an electrical path between a tissue region and a medical device and an inductor, operatively connected to the electrical strand, to significantly reduce currents induced by a changing magnetic resonance imaging electromagnetic field in the electrical strand. The inductor allows a signal corresponding to a measured characteristic of the tissue region to pass therethrough.

Another aspect of the present invention is an electrical lead including an electrical strand to provide an electrical path between a tissue region and a medical device and a RF choke, operatively connected to the electrical strand, to significantly reduce currents induced by a changing magnetic resonance imaging electromagnetic field in the electrical strand. The RF choke allows a therapeutic signal to pass therethrough.

Another aspect of the present invention is an electrical lead including an electrical strand to provide an electrical path between a tissue region and a medical device and a RF filter, operatively connected to the electrical strand, to significantly reduce currents induced by a changing magnetic resonance imaging electromagnetic field in the electrical strand. The RF filter allows a therapeutic signal to pass therethrough.

Another aspect of the present invention is an electrical lead including an electrical strand to provide an electrical path between a tissue region and a medical device and a notch filter, operatively connected to the electrical strand, to significantly reduce currents induced by a changing magnetic resonance imaging electromagnetic field in the electrical strand. The notch filter allows a therapeutic signal to pass therethrough.

Another aspect of the present invention is an electrical lead including an electrical strand to provide an electrical path between a tissue region and a medical device and a bandpass filter, operatively connected to the electrical strand, to significantly reduce currents induced by a changing magnetic resonance imaging electromagnetic field in the electrical strand. The bandpass filter allows a therapeutic signal to pass therethrough.

Another aspect of the present invention is an electrical lead including an electrical strand to provide an electrical path between a tissue region and a medical device and an inductor, operatively connected to the electrical strand, to significantly reduce currents induced by a changing magnetic resonance imaging electromagnetic field in the electrical strand. The inductor allows a therapeutic signal to pass therethrough.

Another aspect of the present invention is an electrical lead including an electrical strand to provide an electrical path between a tissue region and a medical device and a tank circuit, operatively connected to the electrical strand, to significantly reduce currents induced by a changing magnetic resonance imaging electromagnetic field in the electrical strand. The tank circuit allows a signal corresponding to a measured characteristic of the tissue region to pass therethrough.

Another aspect of the present invention is an electrical lead including an electrical strand to provide an electrical path between a tissue region and a medical device and a tank circuit, operatively connected to the electrical strand, to significantly reduce currents induced by a changing magnetic resonance imaging electromagnetic field in the electrical strand. The tank circuit allows a therapeutic signal to pass therethrough.

Another aspect of the present invention is an adapter for a medical device which reduces the effects of magnetic-resonance imaging induced signals. The adapter includes a port to receive a medical device electrical lead capable of providing an electrical path to a desired tissue region; a plurality of coils, each coil generating a voltage due to a changing magnetic-resonance imaging electromagnetic field; the plurality of coils, due to a changing magnetic resonance imaging electromagnetic field, providing a combined voltage that is opposite to the voltage which would be induced by the changing magnetic resonance imaging electromagnetic field in the medical device electrical lead so as to reduce voltages induced by the changing magnetic-resonance imaging electromagnetic field.

Another aspect of the present invention is an adapter for a medical device which reduces the effects of magnetic-resonance imaging induced signals. The adapter includes a port to receive a medical device electrical lead capable of providing an electrical path to a desired tissue region; a coil, the coil generating a voltage due to a changing magnetic-resonance imaging electromagnetic field; the coil, due to a changing magnetic-resonance imaging electromagnetic field, providing a voltage that is opposite to the voltage which would be induced by the changing magnetic-resonance imaging electromagnetic field in the medical device electrical lead so as to reduce voltages induced by the changing magnetic-resonance imaging electromagnetic field.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

Figure 1:
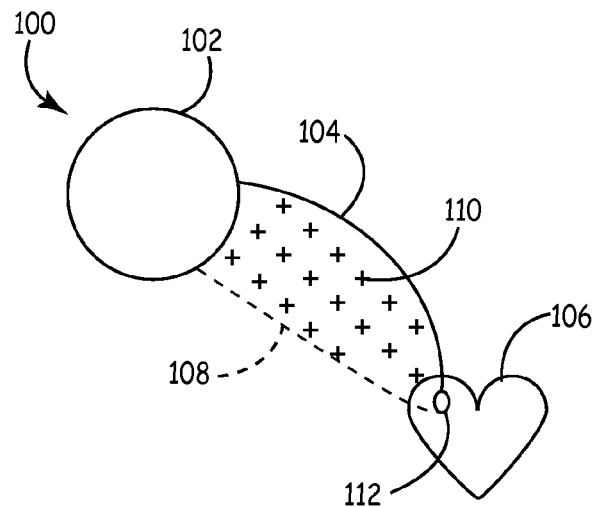
FIG. 1 is a schematic of an implanted pacemaker arrangement in a body.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention as defined by the appended claims.

For a general understanding of the present invention, reference is made to the drawings. In the drawings, like reference have been used throughout to designate identical or equivalent elements. It is also noted that the various drawings illustrating the present invention are not drawn to scale and that certain regions have been purposely drawn disproportionately so that the features and concepts of the present invention could be properly illustrated.

FIG. 1 is a schematic showing a typical pacemaker arrangement 100. The pacemaker comprises a pulse generator canister 102 housing a power supply (not shown) and electronic components (not shown) for sensing and producing electrical pacing pulses. The pulse generator canister 102 has connected to it insulated conductive leads 104 that pass through the body (not shown) and into the heart 106. Conventional bipolar pacemaker leads have two conductive strands, one for pacing and sensing, and the other for ground. The path of the leads 104 is generally not straight. The leads 104 have one or more electrodes 112 in contact with the heart 106. The direct line 108 from the heart 106, where the electrodes 112 are placed, to the generator canister 102 represents a conductive path comprising body tissue (not shown) and fluids (not shown). The completed loop from the pacemaker canister 102, through the leads 104, and back to the pacemaker canister 102 along the path 108 is subject to Lenz's law. That is, a changing magnetic field 110 through the area enclosed by the completed loop (from the pacemaker canister 102, through the leads 104, and back to the pacemaker canister 102 along the path 108) can induce unwanted voltages in the leads 104 and across the heart 106.

In one embodiment of the present invention, and referring to FIG. 1, the pacemaker canister 102 is made out of a non-conductive material. In another embodiment, the canister 102 is coated or covered with various non-conductive insulating materials. This increases the overall resistance of the conductive path loop and thus reduces the voltage across the tissue between electrodes 112 and the canister 102.

Using a three-strand lead design allows for the separation of the pacing signals from the sensing signals and allows for different filtering techniques to be utilized on each separate conductive strand: one strand for the pacing signal for stimulating the heart, one conductive strand for the sensing of the heart's electrical state, pre-pulse, ecg, etc., and one strand for the ground path. Current bi-polar designs use only two conductive strands. This means that the pacing and the sensing signals are carried on the same strand.

For example, in conventional bipolar pacemaker leads, the pacing signal goes "down" (from generator canister to heart) the pacing lead (conductive strand) while the sensing signal travels "up" (from heart to generator canister) the pacing lead. This is the "standard" bipolar pacing setup. If a filter is added to the pacing/sensing strand to block the switch gradient induced signal caused by a magnetic-resonance imaging system, the pacing pulse/signal must travel through the filter, thereby distorting the pacing pulse.

According to the concepts of the present invention, by adding a third conductive strand, a diode, for example, can be put on the pacing strand and one or more filters can be put on the sensing strand. The filters on the sensing lead may be at the distal end of the pacemaker lead or in the generator canister. Thus, by using separate strands, the present invention is able to utilize different kinds of filters (RF filters, high/low pass filters, notch filters, tank circuit, etc.) or other electronics in conjunction with each strand depending on the different signal characteristics and/or signal direction along the conductive strand.

Figure 2:
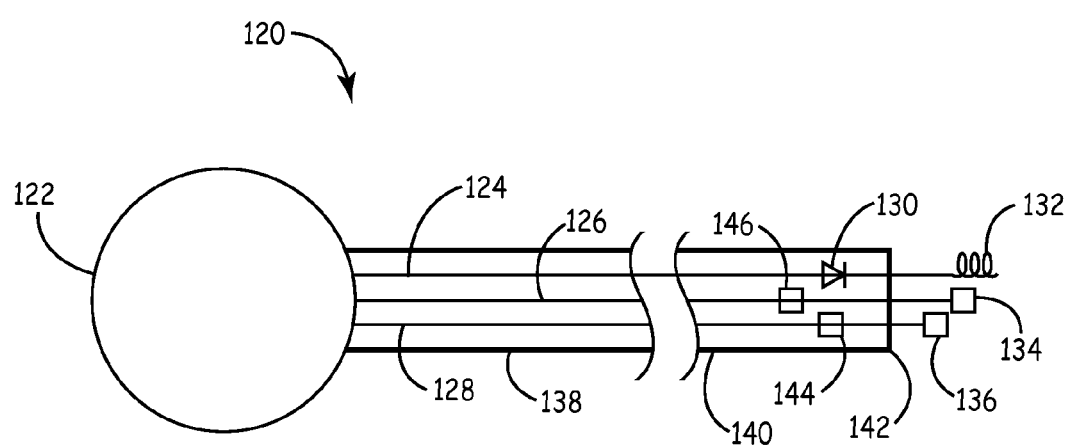
FIG. 2 is a schematic of a pacemaker lead comprising three conductive strands.

FIG. 2 shows a schematic of a pacemaker arrangement 120 including a generator canister 122 containing a pacing pulse generator (not shown), sensing electronics (not shown) and other electronic components (not shown). Attached to the generator canister 122 is a lead assembly 140 having three conductive strands 124, 126, and 128 through lumen 138. Each of the conductive strands 124, 126, and 128 pass through the distal tip 142 of the lead assembly 140 to exposed electrodes 132, 134, and 136, respectively. The exposed electrodes 132, 134, and 136 are placed in contact with or next to the heart.

Conductive strand 124 and electrode 132 are used to deliver pulses to the heart from a pacing generator within the canister 122. Conductive strand 126 and electrode 134 are used as a ground. Conductive strand 128 and electrode 136 are utilized for sensing the electrical signals generated by the heart. In this way, the sensing functionality of pacemakers can be separated from the delivery of pacing pulses.

To block any induced voltage signals from the magnetic-resonance imaging system's changing magnetic fields (the RF or the gradient fields) from propagating along the conductive pulse delivery strand 124, a diode 130 is inserted into the conductive strand 124 near the distal tip of the lead assembly 142. It is noted that the diode 130 can also be is placed in the generator canister 122.

With respect to FIG. 2, other electronic components (i.e. RF Chokes, notch filters, tank circuits, etc.) may be placed into the other conductive strands 126 and 128 shown as by components 146 and 144, respectively. It is noted that a tank circuit is a parallel resonant circuit containing only a coil and a capacitor wherein both the coil and capacitor store electrical energy for part of each cycle. It is further noted that these optional electronic components 146 and 144 can be placed in the generator canister 122.

Optional electronic components 146 and 144 are used to block or significantly reduce any unwanted induced signals caused by the magnetic resonance imaging system from passing along conductive strands 126 and 128 respectively while allowing the desired sensing signals from the heart to pass along conductive strand 126 to electronics in the generator canister 122.

Figure 3:
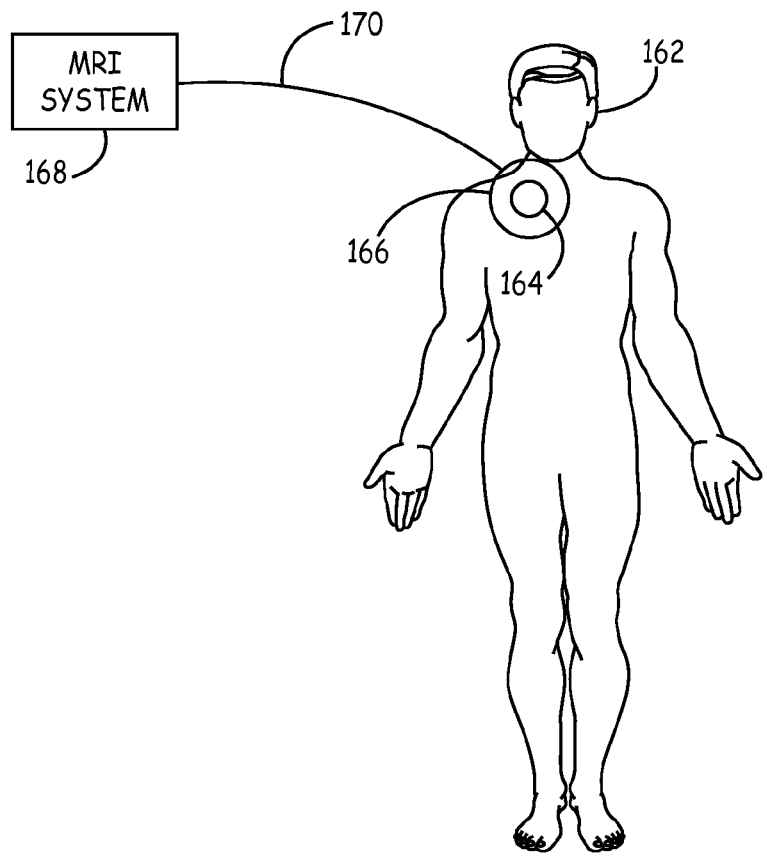
FIG. 3 is a schematic of a sensing system used with a pacemaker.

FIG. 3 is a schematic of an embodiment of the present invention. As illustrated in FIG. 3, a patient 162 is located within a magnetic-resonance imaging system 168, wherein the patient 162 has an implanted heart pacemaker pulse generator canister 164. A surface sensor/transceiver 166 is placed on the exterior of the patient's body 162 over or near the location of the implanted pacemaker generator 164. The sensor/transceiver 166 is in communication with the magnetic-resonance imaging system 168 via communication line 170, which may be a magnetic-resonance imaging safe cable such as a fiber optical cable. Additionally, the sensor/transceiver 166 is in communication with the implanted pacemaker pulse generator canister 164. The means of communication between the sensor/transceiver 166 and the implanted pacemaker generator 164 may be acoustic, optical, or other means that do not interfere with the imaging capabilities or image quality of the magnetic-resonance imaging system. The signals may be digital or analog.

Moreover, with respect to this embodiment of the present invention, a transmitter/receiver is placed in the pacemaker canister 164 so that the magnetic-resonance imaging system 168 can be in operative communication with the pacemaker system and vice versa. Thus, the pacing system can transmit signals to the magnetic-resonance imaging system 168 indicating when the pacemaker is about to deliver a pacing pulse to the heart. The transmitted signals may be digital or analog. In response to this transmitted signal, the magnetic-resonance imaging system 168 stops or pauses the magnetic resonance imaging switched gradient field (imaging scanning sequence) to allow the pacing pulse to occur. After the pacing pulse has been delivered to the heart, the magnetic-resonance imaging system 168 resumes or begins a new imaging scanning sequence.

In another mode of operation, the magnetic-resonance imaging system 168 sends signals to the implanted heart pacemaker pulse generator canister 164 through the sensor/transceiver 166 indicating the application of switched gradient fields. The pacemaker may use this information to switch filters or other electronics in and out of the circuit to reduce or eliminate voltages induced in the pacemaker leads by the gradient fields. For example, the pacemaker may switch in additional resistance or inductance or impedance into the pacing/sensing and/or ground strands based on the signal from the magnetic-resonance imaging system 168 signifying the application of the gradient fields.

In another configuration, there is no surface sensor/transceiver or communication line to the magnetic-resonance imaging system 168. Instead, there is a special sensor in the implanted heart pacemaker pulse generator canister 164 that can sense the application of the gradient fields. In response thereof, the pacemaker switches into the electrical circuit of the pacing/sense and/or ground leads a charging source which is used to charge the implanted heart pacemaker pulse generator canister 164, leads, and/or electrodes to an electrical potential opposite to that which would be induced by the gradient fields. In this way, the induced voltages caused by the gradient fields are cancelled out or reduced to a safe level, by the application of this voltage source.

In a preferred embodiment of the present invention, the charging/voltage source receives its power from inductively coupling to the magnetic-resonance imaging system's RF field. The oscillating RF field supplies power to charge special capacitors in the implanted heart pacemaker pulse generator canister 164. It is noted that other external power sources can be used to power the charging/voltage source in the implanted heart pacemaker pulse generator canister 164.

Figure 4:
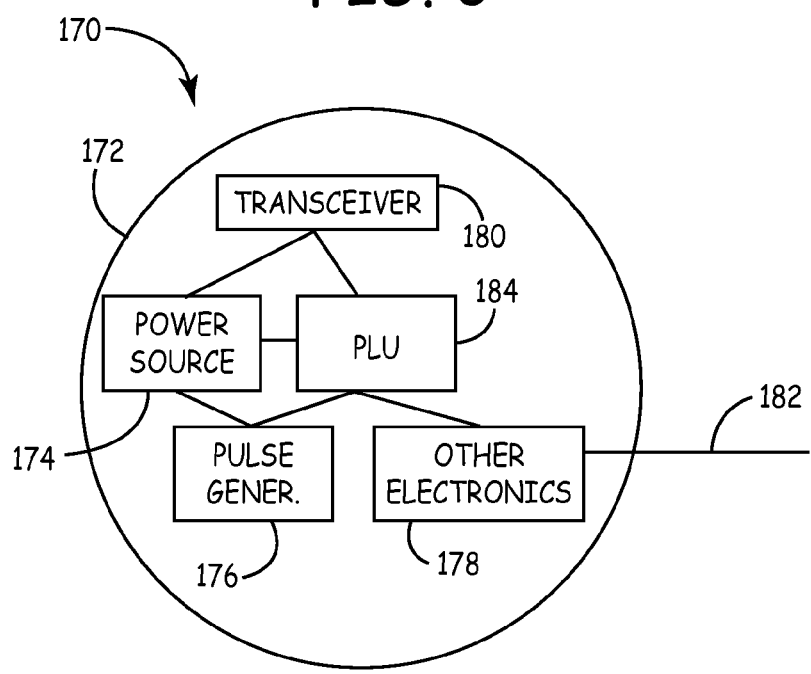
FIG. 4 illustrates an embodiment of a pacemaker canister according to the concepts of the present invention.

FIG. 4 is a diagram of an assembly 170 for the pacemaker generator components comprising the canister housing 172, a programmable logic unit (PLU) 184, a power source 174, and a pulse generator 176. Additionally, means for communicating with an external sensor/transceiver is provided by transceiver 180. Other electronic components 178; e.g., signal filters, signal processors, lead connectors, etc. are also located in the canister 172. The pacing leads 182 pass through the canister 172 and connect to the internal electronics 178. During a magnetic-resonance imaging examination, the signals transmitted and received by the transceiver 180 may be used to synchronize the magnetic resonance imaging system's scanning sequences with the delivery of the pacing signals.

Figure 5:
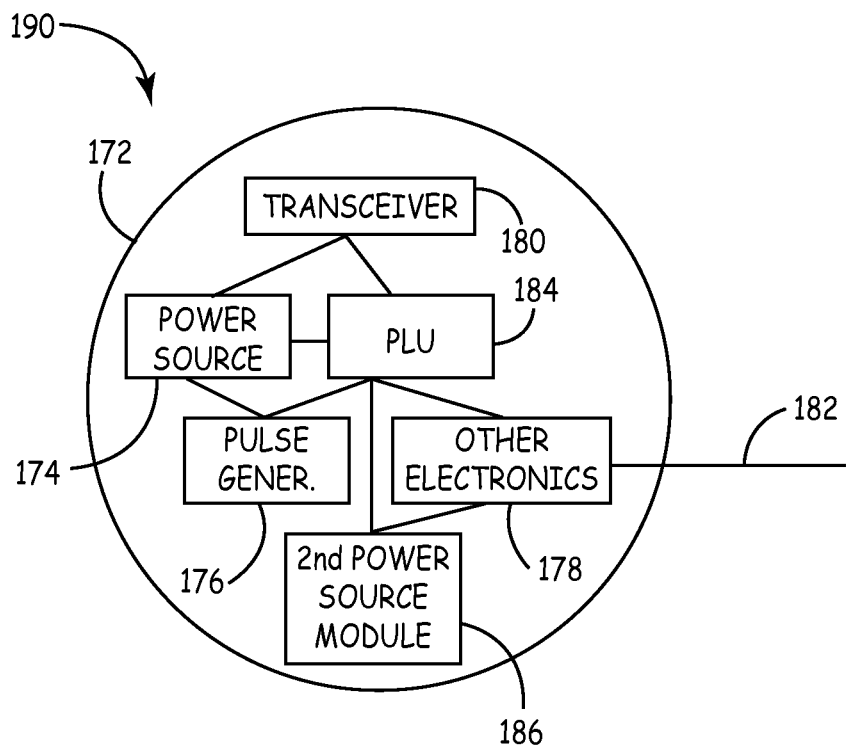
FIG. 5 illustrates another embodiment of a pacemaker canister according to the concepts of the present invention.

In another embodiment, as depicted in FIG. 5, the pacing generator assembly 190 further includes a second power module 186 which may be an inductive coil and/or capacitor bank, suitable for capturing and storing power from the magnetic-resonance imaging system's transmitted RF signal.

In one embodiment, the power stored in the power module 186 is used to develop an electrical potential in the leads 182 that is opposed to that which is induced by the application of the magnetic-resonance imaging system's gradient fields.

Figure 21:
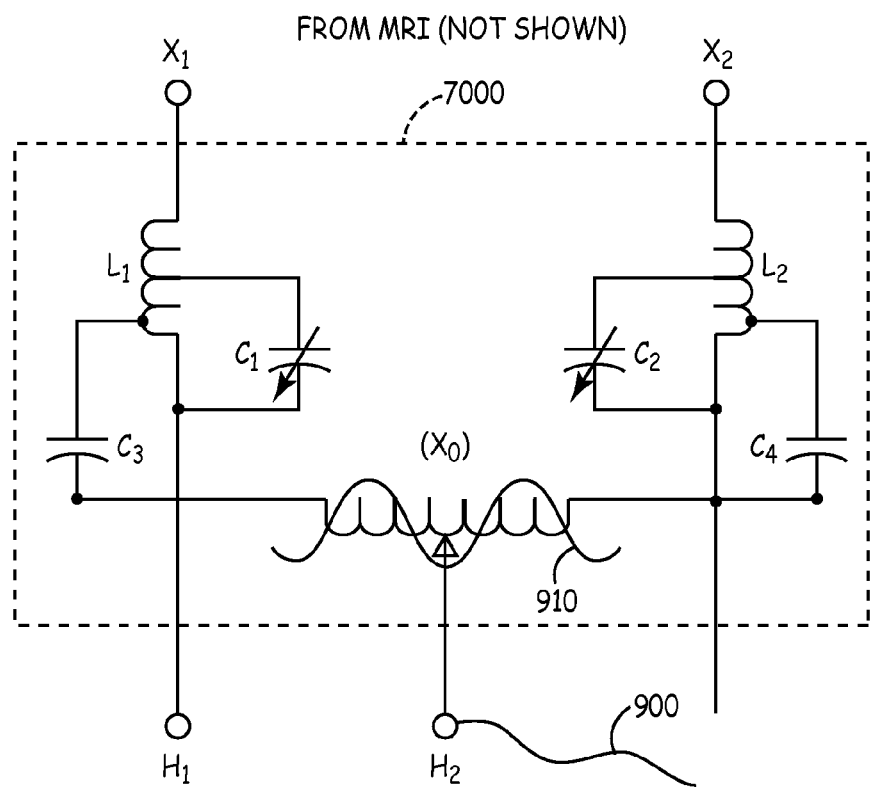
FIG. 21 is a circuit diagram representing a capacitance unbalanced balun unit according to the concepts of the present invention.

FIG. 21 further illustrates a common-mode feedback circuit 400. The common-mode feedback circuit is similar as those in conventional fully differential operational amplifiers. The common-mode amplifier 400 amplifies the difference between the output common-mode voltage (voutp+voutn)/2 and the desired output common-mode voltage. The output of the common-mode amplifier 400 provides negative feedback to controls the current sources 210 and 220 to keep the output common-mode voltage constant.

Alternatively, the output of the common-mode amplifier 400 may control the current sources 230 and 240. The common-mode feedback can be engaged during all or any of the segments. It is preferred that the common-mode feedback be engaged during the first segment only while keeping current source 220 constant and matched to current source 240.

In another embodiment, the power stored in the power module 186 is used to operate various switches in the electronics module 178 which may switch in or out various power serge protection circuits in-line and/or signal filters to the leads 182.

In a further embodiment, and referring to FIG. 5, the module 186 may be used to electrically charge the pacemaker canister 172, which is made of a conductive material, in synchronization with the application of the magnetic resonance imaging system's gradient fields so that the electrical potential difference between the pacing electrodes and the pacemaker canister 172 is reduced. That is, the sum of the induced voltage difference due to the application of the gradient fields plus the voltage difference due to the application of the electrical charge stored in the power module 186 results is a net voltage significantly below any threshold level, above which a problem may develop.

Figure 6:
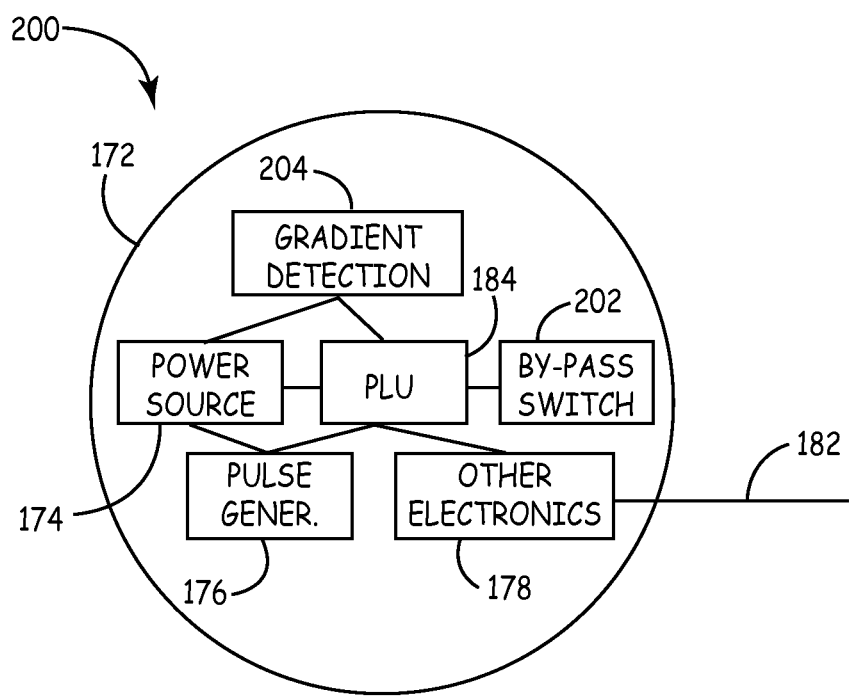
FIG. 6 illustrates a further embodiment of a pacemaker canister according to the concepts of the present invention.

FIG. 6 depicts another assembly 200, which includes the basic components of FIG. 5 less the transceiver 180, a gradient field detector 204, and a by-pass switch component 202. By detecting the gradient signal in the pacemaker canister 172 with gradient field detector 204, the pacemaker can switch filters and/or other electronics 178 in or out of the circuit.

In one embodiment, when no gradient fields are detected, the switch 202 is closed to by-pass the electronics component 178, which may be a combination of low-pass, high-pass, notch filters, diodes, and/or other electronics. In this mode (switched closed), the pacing pulse (and sensing signals) by-pass the filters components 178. When gradient field detector 204 detects the gradient signals, the switch 202 is opened and any gradient fields induced signals in the leads 182 are blocked or significantly reduced by the filters components 178. In the open mode, the pacing and sensing signals pass through the filters component 178 as well.

The gradient detector 204 may communicate the sensing of the gradient field to other components in the pacemaker via its connection to the PLU 184 so that the pacing signal can be modified, if necessary, to compensate for any distortion it may suffer by now going through the filters component 178. Additionally, the sensing signal, now also passing through the filter components 178 may be distorted. This may be compensated for by including signal recovery/reconstruction logic into the PLU or into a separate signal-processing component.

Referring back to FIG. 1, by increasing the impedance of the leads 104, the voltage across the tissue gap from the electrodes 112 and the pacemaker canister 102 can be reduced. Inserting a resistor or using a higher resistive wire for the pacemaker leads 104 will reduce the current induced in the current loop, which includes the virtual loop portion across the (heart 112) tissue to the pacemaker generator canister 102.

By using various inductors in-line with the various leads 104, it is possible to make the leads 104 have a high impedance for the low frequency magnetic-resonance imaging gradient fields frequency and a low impedance for the magnetic-resonance imaging system's RF frequency. Alternatively, different impedances (inductors/resistors/capacitors) may be switched in-line or out of the leads' circuitry depending on the timing and application of the gradient and/or RF fields.

In another embodiment, not shown, the pacemakers' electronics can be augmented to include one or more digital signal processors. By converting the sensing signal into a digital signal, the digital signal processor (DSP) can reconstruct the sensing signal after it has passed through filters and has been distorted by the filtering or other elements that may have been added to the lead circuit. The DSP may also be used to reject any signals that do not have a correct cardiac signature, thus rejecting any signals caused by the switched gradient fields, which is a non-cardiac signal.

In another embodiment of the present invention, a pacemaker lead or other medical device, having a long conductive lead and functioning in an magnetic-resonance imaging environment, may be configured, according to the concepts of the present invention, to include additional loops to cancel the induced voltage effects in the leads of the original current loop formed by the leads.

In a further modification of the present invention (not shown), an electrical lead component for a medical device includes an electrical lead that provides an electrical path to a desired tissue region. The electrical lead component further includes a voltage source, such as a battery or capacitor and a sensor to sense voltages induced by the changing magnetic-resonance imaging electromagnetic field. A switching device, connected to the sensor and voltage source, connects the voltage source to the electrical lead in response to the sensed voltage induced by the changing magnetic-resonance imaging electromagnetic field such that the voltage source provides a voltage that is opposite to the voltage which would be induced by the changing magnetic resonance imaging electromagnetic field in the medical device electrical lead so as to reduce voltages induced by the changing magnetic-resonance imaging electromagnetic field. The electrical lead component further includes a variable resistor connected to the voltage source to regulate an amount of voltage being provided. The changing magnetic-resonance imaging electromagnetic field is a magnetic-resonance imaging switched gradient field or a magnetic-resonance imaging switched gradient field.

Additionally, the present invention may be modified (not shown) so that a medical device that is capable of providing medical treatment to a desired tissue region is associated with a voltage source and a sensor to sense voltages induced by the changing magnetic-resonance imaging electromagnetic field. A switching device, connected to the sensor and voltage source, connects the voltage source to the medical device in response to the sensed voltage induced by the changing magnetic-resonance imaging electromagnetic field such that the voltage source provides a voltage that is opposite to the voltage which would be induced by the changing magnetic-resonance imaging electromagnetic field in the medical device so as to reduce voltages induced by the changing magnetic resonance imaging electromagnetic field. The medical device is further associated with a variable resistor connected to the voltage source to regulate an amount of voltage being provided. The changing magnetic-resonance imaging electromagnetic field is a magnetic-resonance imaging switched gradient field or a magnetic-resonance imaging switched gradient field.

Figure 7:
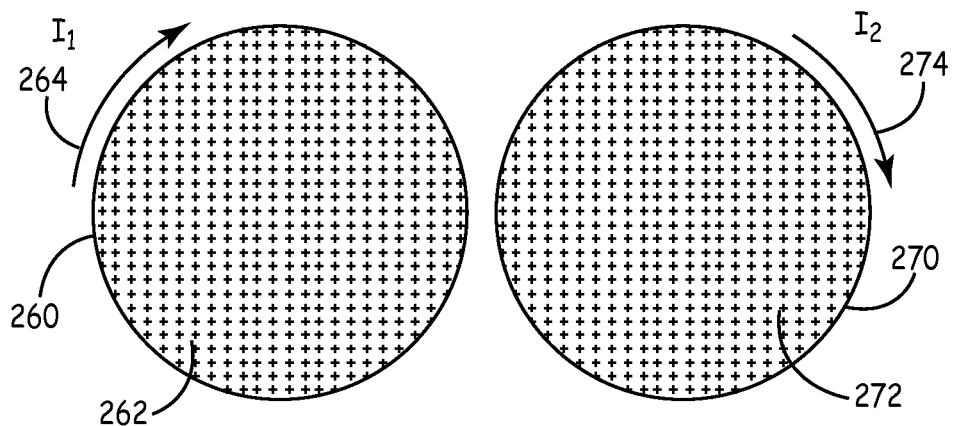
FIG. 7 is an illustration of inductive currents in conductor loops.

In FIG. 7, two conductive loops 260 and 270 having the same amount of area and in the same plane, positioned in a changing magnetic field 262 and 272, develop currents 264 and 274. In FIG. 7, both induced currents I1 and I2 travel in the same direction (clockwise direction shown) at all times as the magnetic field 262 and 272 oscillate.

Figure 8:
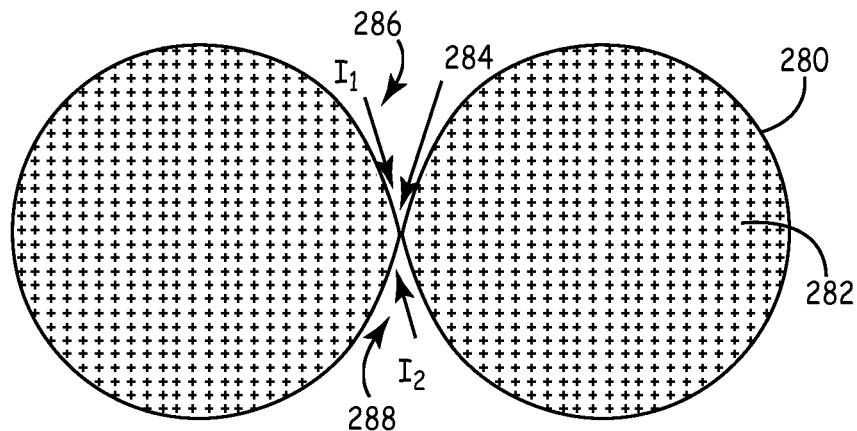
FIG. 8 is an illustration of canceling inductive currents in conductor loops according to the concepts of the present invention.

FIG. 8 shows that by connecting the two conductive loops 260 and 270 of FIG. 7 to form a single conductor 280, the currents induced in each lobe can be made to cancel each other out. The two loops are connected so that a single conductor is formed which crosses over itself at 284. In this case, as shown in FIG. 8, the two currents 286 and 288 cancel each other out resulting in net current of zero magnitude around the conductor 280. This type of configuration of conductors in a changing magnetic field may be used to cancel induced currents in the conductors.

Figure 9:
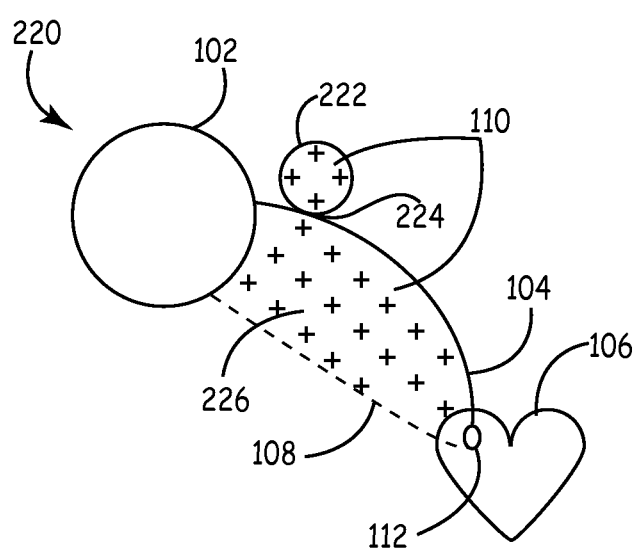
FIG. 9 is a schematic of an embodiment of a pacemaker lead utilizing inductive loops according to the concepts of the present invention.

FIG. 9 depicts an implanted pacemaker system 220 comprising a pacing generator canister 102, conductive leads 104, and electrodes 112 positioned in the heart 106. Additional loops 222 are added to the overall configuration of the lead 104 in the body with one or more crossings 224. In accordance with the concepts of the present invention, the plane of the loop 222 is in the same plane as defined by the rest of the lead geometry.

The same oscillating magnetic field 110 passes through loop 222 and the loop defined by generator canister 102, conductive leads 104, electrodes 112, and conductive path 108 through the body from the heart 106 to the generator canister 102. It is noted that the total area enclosed by the loops can be adjusted by adding or removing loops 222 or by changing the area enclosed by the loops (singly or collectively).

In one embodiment, the total area of the loop 222 is the same as the loop area 226. In another embodiment, the total area of the loop 222 is different from loop area 226. In another embodiment, the plane of loop 222 is different from the plane of loop area 226. In yet another embodiment, loop 222 and/or loop area 226 do not define a single plane but are curved in three different spatial directions. In yet another embodiment, loop 222 consists of at least three loops in three orthogonal planes.

Figure 10:
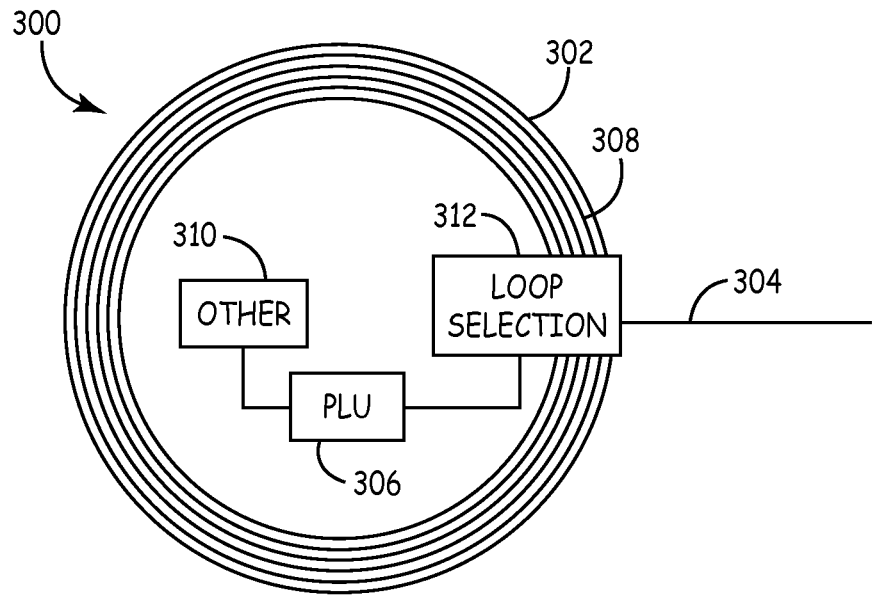
FIG. 10 is a schematic of an embodiment of inductive loops in a pacemaker canister according to the concepts of the present invention.
Figure 11:
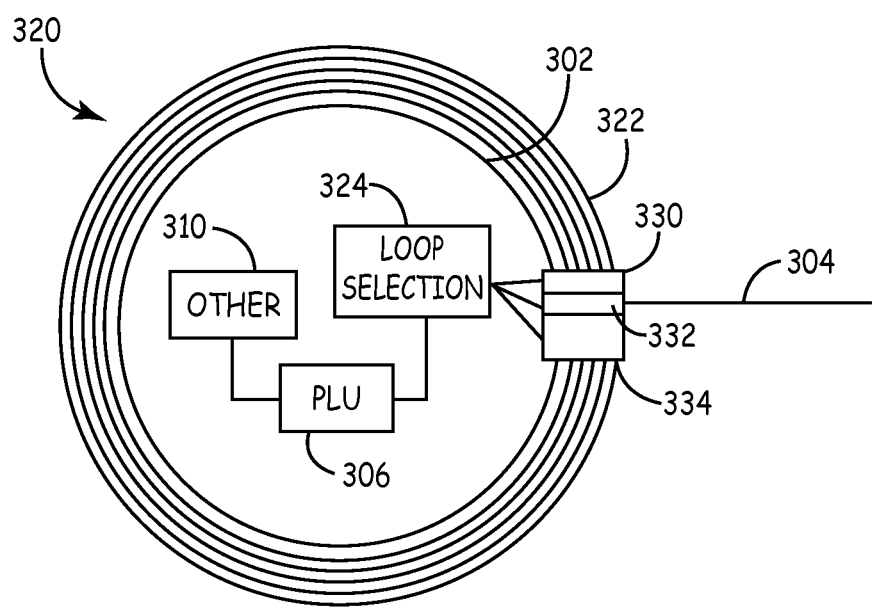
FIG. 11 is a schematic of an embodiment of inductive loops around a pacemaker canister according to the concepts of the present invention.

In a further embodiment, as illustrated in FIG. 11 and will be discussed in more detail below, the new additional loops 222 can be positioned in such a way as to encircle the pacemaker's generator canister 102. In another embodiment, as illustrated in FIG. 10 and will be discussed in more detail below, the additional loops 222 may be positioned inside the pacemaker's generator canister 102.

Referring back to FIG. 9, a fastener (not shown) can be used at the loop cross over point 224 to allow for adjustment of the loop's enclosed area and/or orientation and, once adjusted, to lock in the loop's adjustments. This same fastener can also be used to adjust a plurality of loops.

In another aspect of the present invention, a selection mechanism can be included in the pacemaker system. This selection mechanism is used to adjust the number of loops to include in the circuit.

For example, if the loops are located within the pacemaker canister, the selection mechanism can be used to manually select how many loops to include in the lead circuit depending on where the pacemaker can is placed in the body and the length of the lead. Alternatively, the selection mechanism may be used to automatically select how many loops to include in the lead circuit depending on where the pacemaker can is placed in the body and the length of the lead. In this alternative embodiment, the present invention monitors the voltages on the pacemaker's lead(s) and selects a different number of loops to connect to the lead(s) to cancel any induced voltages. Lastly, the selection mechanism may be externally programmed and transmitted to the pacemaker's PLU that then monitors and adjusts the number of loops in the lead circuit.

FIG. 10 is a schematic of a pacemaker system 300 that includes a pacemaker canister 302 and the pacemaker's leads 304. The pacemaker's canister 302 contains a programmable logic unit (PLU) 306, and other electronics 310, e.g. a pulse generator, power supply, etc. The system 300 further includes conductive loops 308 positioned within the pacemaker canister 302.

The conductive loops are connected to a loop selection component 312 that provides means for selectively adjusting the number of loops to be included in the leads' circuit 304. The leads 304 are also connected to the loop selection component 312 so that the leads 304 can be electrically connected to the loops 308.

The loop selection component 312 connects the loops 308 to the leads' circuit 304 in such a way that any induced voltages in the loops 308 caused by changing magnetic fields in the environment, e.g. an magnetic resonance imaging environment, will cancel out or significantly reduce in magnitude any induced voltage along the leads 304 that have also been caused by the environment's changing magnetic fields.

In one embodiment, the loop selection component 312 is adjusted manually by screws, connection pins, and/or other means.

In another embodiment, the loop selection component 312 is controlled by the PLU 306. The PLU 306 may include means for receiving loop selection instructions from an external transmitter or may include sensors that measure environmental variables, e.g. changing magnetic fields in an magnetic-resonance imaging environment. From this information, the PLU 306 dynamically adjusts the loop selection component's 312 adjustable parameters so as to change which loops are included in the leads' circuitry 304.

It is noted that the loops 308 need not be all in the same plane.

FIG. 11 is a schematic of another pacemaker system 320. Pacemaker system 320 includes conductive loops 322 positioned externally to a pacemaker canister 302. In this embodiment, the loops 332 are connected to an input port connection 330 and to an output port connection 334 which are electrically connected to the loop selection component 324 located inside the pacemaker canister 302. Additionally, the pacemaker leads 304 are connected to an electrical connector 332 that is electrically connected to the loop selection component 324. It is noted that the conductive loops 322 need not be all in the same plane.

Figure 12:
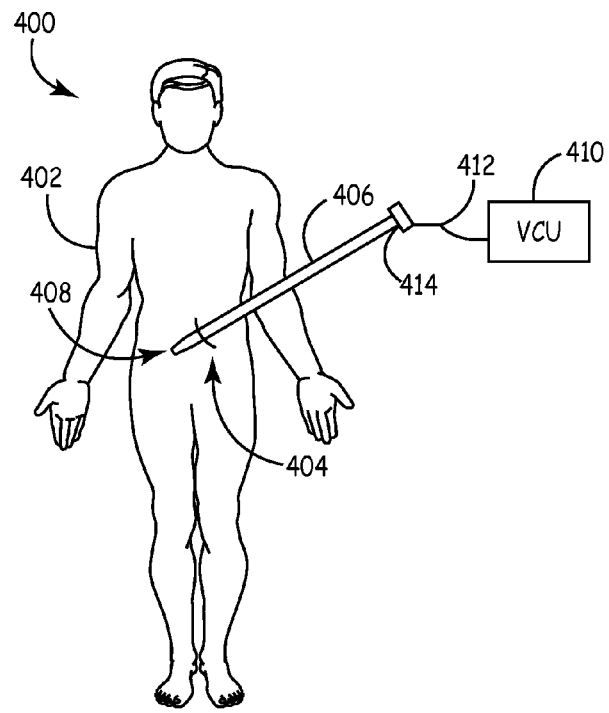
FIG. 12 illustrates of an embodiment of a medical device with an external voltage cancellation unit according to the concepts of the present invention.

FIG. 12 depicts a medical procedure in which a catheter 406 or other medical device, e.g. a guidewire, which is comprised of conductive leads or other conductive components, may be partially inserted into a body 402 and partially external to the body. In an magnetic-resonance imaging environment, such conductive medical devices 406 can develop problems like heating, induced voltages, etc. caused by the changing magnetic fields of the magnetic-resonance imaging system. To compensate for induced currents and/or induced voltages in such devices 406, a voltage compensation unit (VCU) 410 is electrically connected to the medical device 406 via conductive leads 412 and electrical connectors 414, externally to the patient's body 402.

The medical device 406 is constructed with additional electrical connectors 414 to allow for easy attachment of the VCU device 410. The VCU device 410 is connected to a power supply or may have a built in power supply, e.g. batteries. The VCU device 410 has sensors built into it, which monitor the voltages of the conductive components in the medical device 406, and delivers opposing voltages to the medical device 406 to cancel out or significantly reduce any induced voltages caused by the changing magnetic fields in an magnetic resonance imaging (or other) environment.

Additionally or alternatively, the VCU device 410 has sensors to detect the changing magnetic fields of the magnetic-resonance imaging system and can synchronize the application of the canceling voltage with the magnetic-resonance imaging System's changing fields.

Figure 13:
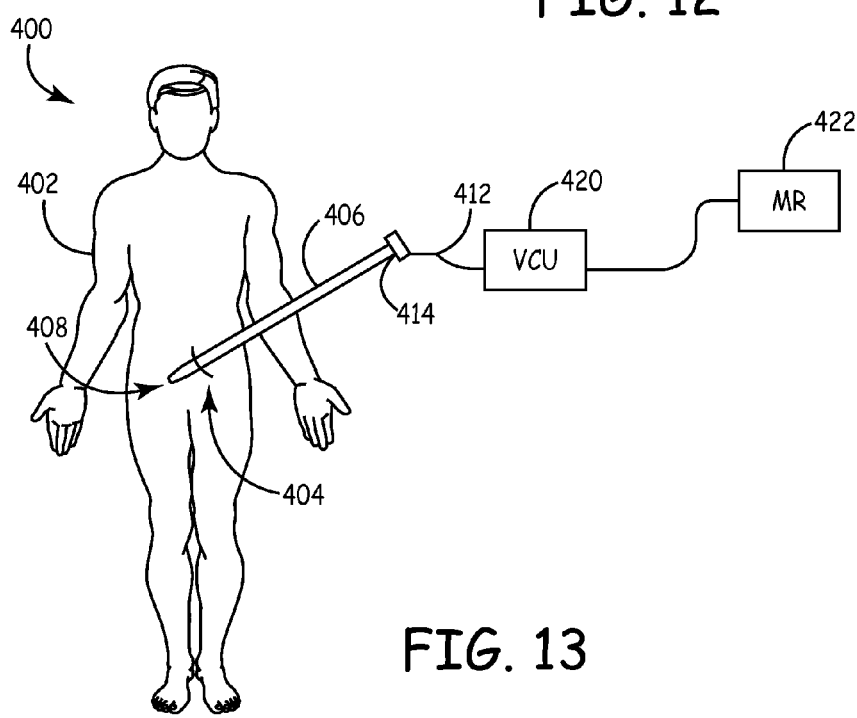
FIG. 13 illustrates of another embodiment of a medical device with an external voltage cancellation unit according to the concepts of the present invention.

In another embodiment depicted in FIG. 13, the VCU device 420 is connected to the magnetic-resonance imaging system 422 via communication means 424 so that the start and end of the application of the magnetic-resonance imaging system's 422 fields may be communicated to the VCU device 420. Other information that may be required (field strengths to be applied, magnetic resonance imaging scan sequence, etc.) may also be communicated to the VCU device 420. The communication means 424 may be electrical wires/coaxial/shielded/other, optical fiber, or an RF transmitter/receiver, or some sonic means of communication.

The conductive lead of a heart pacemaker is a filer winding. The filer winding may consist of two or more conductive stands coiled together in a spring-like configuration. The current (pulses, signals) then flows over the surface and through the contact points between one loop and the adjacent loop of the winding, rather than following the windings of the individual conductive strands. This occurs because there is no significant insulating material or surface coating between the contact points of the windings.

In accordance with the present invention, to reduce the alternating, induced current flowing, caused by a magnetic resonance system's changing magnetic fields, through the, for example, pacemaker's winding leads, the inductance value of the pacemaker's lead may be changed to increase the overall impedance of the pacemaker's lead.

Thus in one embodiment, a suitable RF choke is inserted inline with the pacemaker's lead, preferable near the distal tip. For example, referring back to FIG. 2, and to the embodiment therein, electronic component 146 and/or 144 may comprise an RF choke. In a preferred embodiment, the RF choke has an inductance value of about 10 microHenries. In another embodiment, the inductance value is about 2 microHenries.

The specific value of inductance to introduce into the, for example, pacemaker's lead depends in part on the frequency of the induced signal from the magnetic-resonance imaging system's imaging sequence that is to be blocked or significantly reduced.

Figure 14:
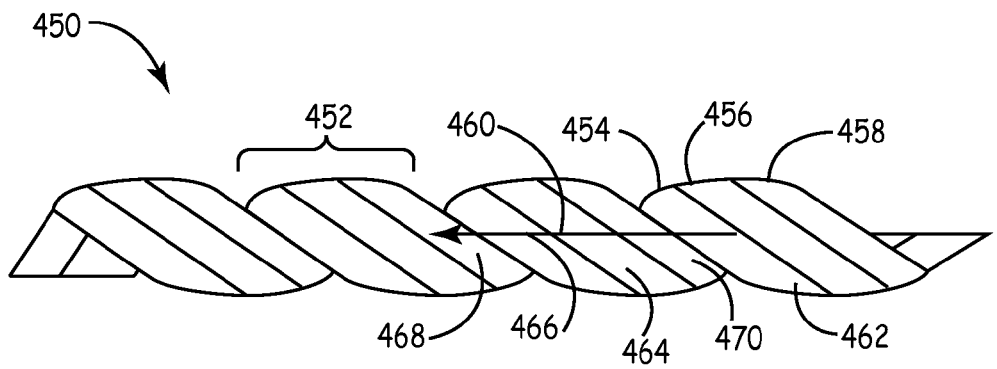
FIG. 14 illustrates a portion of coiled leads used in a medial device according to the concepts of the present invention.

FIG. 14 shows a portion of a coiled multi-filer lead 450. As illustrated in FIG. 14, lead 450 includes a plurality of coil loops 452; each coil loop 452 consists of three conductive strands 454, 456, and 458. A current 460 through the lead 450 can cross contact points 464, 466, and 462 between the strands as well as the coil contact points 468 and 470. Thus, the current 460 does not follow the coiling of the lead's conductive strands 454, 456, and 458.

Figure 15:
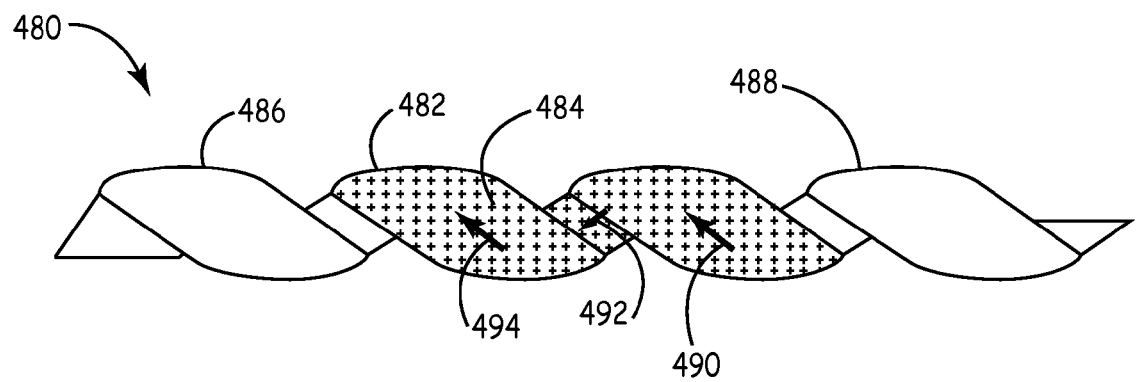
FIG. 15 illustrates another embodiment of a portion of coiled leads used in a medial device according to the concepts of the present invention.

FIG. 15 shows a portion of a coiled lead assembly 480 including a region 482 that has an insulating coating 484 applied to its surface. The coiled lead assembly 480 is depicted in an elongated position in which adjacent coil windings are not in contact with one another. It is to be understood that the normal, relaxed position of the lead assembly 480 has all adjacent coiled windings in contact.

With the addition of an insulated coating 484 over the winding region 482, the current 490, 492, and 494 is now forced to substantially follow the curvature of the coiled winding 482, thus forming an inductive coil inline with the conductive lead regions 486 and 488 which do not have an insulated coating. The inductive value of the created inductor can be adjusted by adjusting the length of the region to which the insulative coating 484 is applied.

It is noted that the coating 484 may be a partially resistive material. In such an example, the inductance is then adjusted by adjusting the resistive properties of the material 484.

Figure 16:
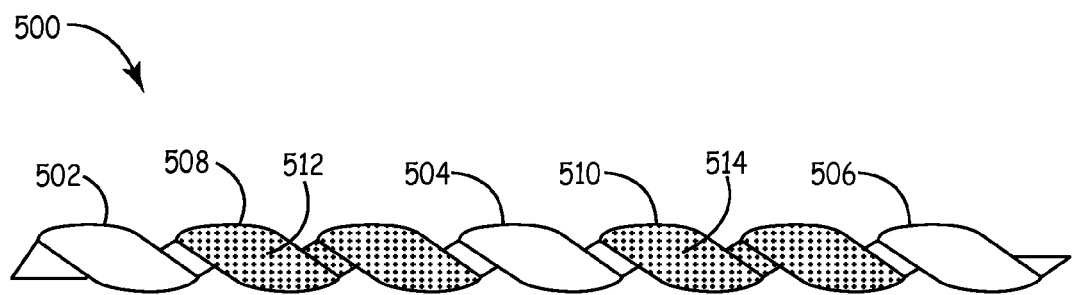
FIG. 16 illustrates a further embodiment of a portion of coiled leads used in a medial device according to the concepts of the present invention.

FIG. 16 is a schematic of a coiled lead assembly 500 comprised of uninsulated regions 502, 504, and 506, and coated insulated regions 508 and 510 with coatings 512, and 514, respectively. Through the application of the coating, the current is forced to substantially follow the curvature of the coiled windings, thus forming an inductive coil inline with the conductive lead regions that do not have a coating applied thereto. The inductive value of the created inductor can be adjusted by adjusting the length of the region to which the insulative coatings 512 and 514 are applied. In one embodiment, coatings 512 and 514 are the same coatings. In another embodiment, the coatings 512 and 514 are different materials.

It is noted that coatings 512 and 514 may be the same coating material but having differing properties, e.g., the thickness of the coatings, or the length of the coated region 508 and 510. It is further noted that the two-coated regions 508 and 510 may have different inductive values. It is also noted that more than two different regions along the length of the lead assembly can be coated.

Figure 17:
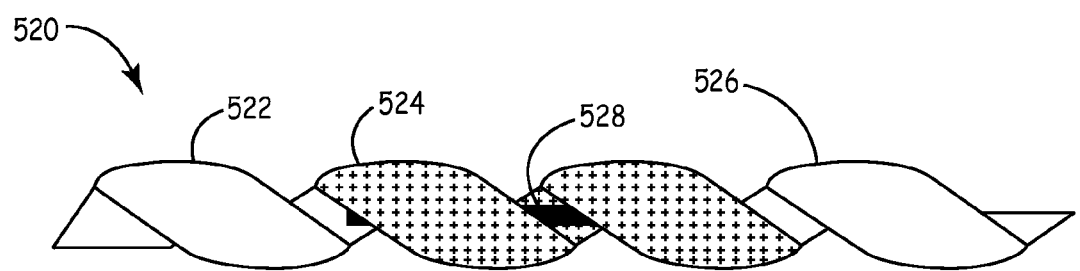
FIG. 17 illustrates another embodiment of a portion of coiled leads used in a medial device according to the concepts of the present invention.

FIG. 17 is a schematic of a portion of a coiled lead assembly 520 including at least one region 524 with a coating applied thereto. Through the application of the coating, the current is forced to substantially follow the curvature of the coiled windings, thus forming an inductive coil inline with the conductive lead regions 522 and 526 that do not have a coating applied thereto.

The inductive value of the created inductor can be adjusted by adjusting the length of the region to which the insulative coating 524 is applied. Additionally, through the coated region 524 is positioned a rod 528 which also changes the inductive value of the coated region 524. It is noted that the rod 528 may be of ferrite material. It is further noted that multiple rods can be inserted into multiple coated regions along the length of the coiled lead.

It is noted that multiple coatings can be applied to the same coated region of the coiled lead wherein the multiple coating layers may be comprised of different materials. It is further noted that one or more layers of the multiple layers of coatings may comprise ferrite material.

In another embodiment of the present invention, the heating and/or induced voltages on catheters or guide wires is controlled or substantially eliminated by introducing or creating detuned characteristic impedance at a proximal ends (ends that are not within the body) of the catheters or guide wires. This introduction or creation of detuned characteristic impedance will be discussed in more detail with respect to FIGS. 18-21.

As noted above, during magnetic-resonance imaging procedures, catheters, and guide wires (wire lines), with or without grounded shielding, are used to measure physiological signals. In such instances, two-wire catheters or guide wires having a grounded shield have one conductor that carries the actual measured signal and the other wire is grounded. In terms of characteristic impedance, the two-wire catheters or guide wires having a grounded shield are unbalanced. In contrast, a single wire catheter or guide wire has characteristic impedance that is balanced.

According to the concepts of the present invention, the characteristic impedance of the catheters and guide wires, used during magnetic-resonance imaging procedures, should be unbalanced at the proximal end, under all conditions, to reduce or eliminate heating and induced voltages. To realize this reduction or elimination of heating and induced voltages at the proximal end of the catheters and guide wires, used during magnetic-resonance imaging procedures, by creating an unbalanced characteristic impedance, the present invention proposes providing a Balun along the catheter and/or guide wire or at the proximal end of the catheter and/or guide wire.

Using a Balun to maintain unbalanced characteristic impedance, the reactance at the distal end of the catheter and/or guide wire approaches infinity. Thus, even when there is some potential on the wire, the unbalanced characteristic impedance has approximately four times the ground loop looses of a balanced line, thereby substantially avoiding any incident of thermal injury. An example of such an arrangement is illustrated in FIG. 18.

Figure 18:
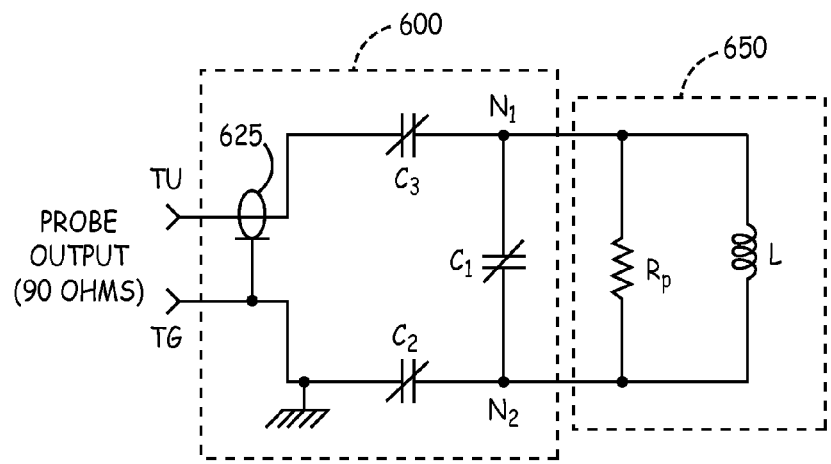
FIG. 18 illustrates a circuit diagram representing a guide wire with an unbalancing impedance circuit according to the concepts of the present invention.

As illustrated in FIG. 18, a guide wire or catheter 650 has characteristic impedance due to its intrinsic resistance from intrinsic resistor capacitors RP and its intrinsic inductance from intrinsic inductor L. To create the unbalanced characteristic impedance at the proximal end of the guide wire or catheter 650, a Balun 600 is placed along the guide wire or catheter 650. In other words, the Balun 600 is in vitro.

The Balun 600 includes a variable capacitor C1 connected in parallel with the guide wire or catheter 650 and two variable capacitors C2 and C3 connected in series with the guide wire or catheter 650. It is noted that one end of the variable capacitor C2 is connected to the shield 625 and ground or a known voltage. The capacitance of the variable capacitors C1, C2, and C3 are adjusted to create the unbalanced characteristic impedance.

More specifically, the variable capacitors C1, C2, and C3 may be used for both matching and providing a certain amount of balancing for the guide wire or catheter characteristic impedance. In this example, the variable capacitors C1, C2, and C3 lift the voltage on the guide wire or catheter 650 from ground. The larger the reactance of the variable capacitors C1, C2, and C3, the more symmetric and balanced the circuit of the guide wire or catheter 650 becomes.

Conversely, according to the concepts of the present invention, if the reactive capacitance of the Balun 600 is detuned (made less resonant), the circuit of the guide wire or catheter 650 becomes asymmetric and unbalanced, breaking down, to reduce the chances of thermal injury at the distal end of the guide wire or catheter 650 due to heating from induced voltages.

Figure 19:
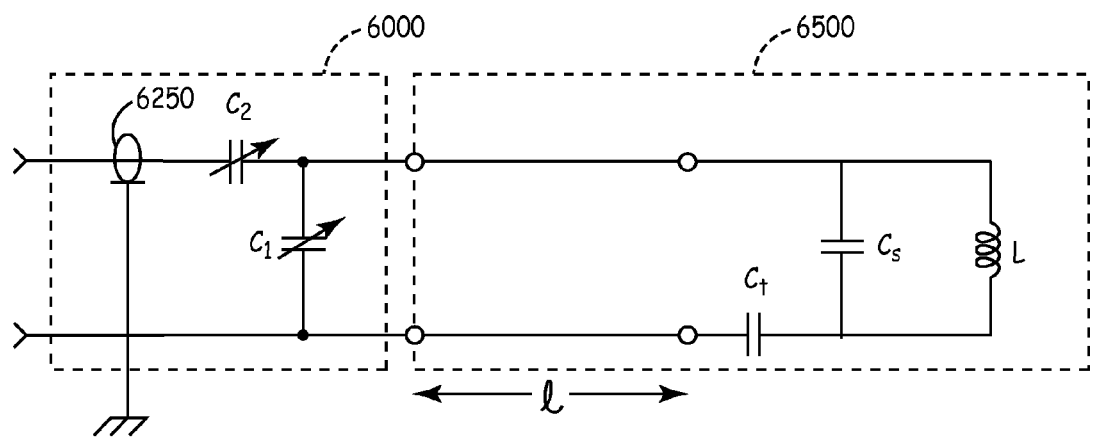
FIG. 19 illustrates another embodiment of a circuit diagram representing a guide wire with an unbalancing impedance circuit according to the concepts of the present invention.

FIG. 19 illustrates another embodiment of the present invention wherein a guide wire or catheter 6500 has characteristic impedance due to its intrinsic capacitance from intrinsic capacitors Ct and Cs and its intrinsic inductance from intrinsic inductor L. To create the unbalanced characteristic impedance at the proximal end of the guide wire or catheter 6500, a Balun 6000 is connected across the proximal end of the guide wire or catheter 6500. In other words, the Balun 6000 is outside the body at the proximal end of the guide wire or catheter 650. By having the Balun 6000 outside the body, the varying of the reactance of the guide wire or catheter 6500 can be readily and manually controlled.

The Balun 6000 includes a variable capacitor C1 connected in parallel with the guide wire or catheter 6500 and a variable capacitor C2 connected in series with the guide wire or catheter 6500. It is noted that one end of the variable capacitor C1 is connected to the shield 6250 and ground or a known voltage. The capacitance of the variable capacitors C1 and C2 are adjusted to create the unbalanced characteristic impedance.

More specifically, the variable capacitors C1, and C2 may be used for both matching and providing a certain amount of balancing for the guide wire or catheter 6500 characteristic impedance. In this example, the variable capacitors C1, C2, and C3 lift the voltage on the guide wire or catheter 6500 from ground. The larger the reactance of the variable capacitors C1 and C2, the more symmetric and balanced the circuit of the guide wire or catheter 6500 becomes.

Conversely, according to the concepts of the present invention, if the reactive capacitance of the Balun 6000 is detuned (made less resonant), the circuit of the guide wire or catheter 6500 becomes asymmetric and unbalanced, breaking down, to reduce the chances of thermal injury at the distal end of the guide wire or catheter 6500 due to heating from induced voltages.

Figure 20:
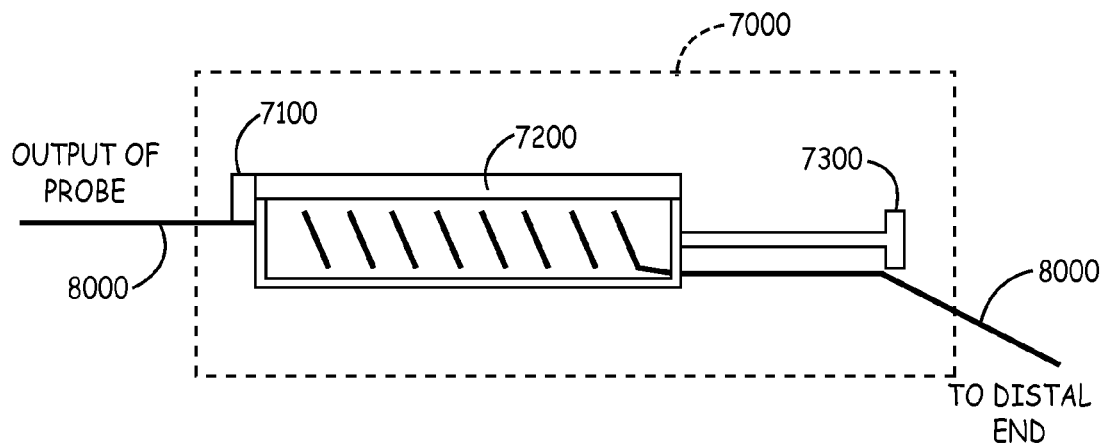
FIG. 20 illustrates a balun used in conjunction with a guide wire according to the concepts of the present invention.

FIG. 20 illustrates a further embodiment of the present invention wherein a guide wire or catheter 8000 is connected to a Balun 7000. The Balun 7000 includes a variable capacitor 7100, a copper foil 7200, and a non-conductive tuning bolt 7300. The Balun 7000 is further connected to the output of the probe 8000.

The Balun 7000 adjusts its characteristic impedance by increasing or decreasing the number wire coils are found within the copper foil 7200. The combination of the coils and the copper foil 7200 forms a variable capacitor, having it impedance determined by the change in the surface area of the coils positioned opposite of the copper foil 7200. As more coils are introduced into the volume created by the copper foil 7200, the capacitance of this combination increases. Moreover, as fewer coils are introduced into the volume created by the copper foil 7200, the capacitance of this combination decreases. Thus, the capacitance of the Balun 7000 is adjusted to create the unbalanced characteristic impedance.

FIG. 21 illustrates another embodiment of the present invention wherein a guide wire or catheter 900 is electronically isolated by a voltage control unit to always appear as an unbalanced line to any possible magnetic field that may be applied from a magnetic resonance imager unit (not shown). As current begins to flow due to the changing magnetic fields from the magnetic resonance imaging, a tapped voltage from a voltage-controlled oscillator in the magnetic resonance imaging unit is applied across terminals X1 and X2 of the voltage control unit.

According to the concepts of the present invention, to automatically maintain an unbalanced characteristic impedance at the distal end of the guide wire or catheter 900, a capacitance unbalanced balun unit 7000, located within the voltage control unit, is connected through a variable inductor 910 to the proximal end of the guide wire or catheter 900. In other words, the voltage control unit containing the capacitance unbalanced balun unit 7000 is outside the body at the proximal end of the guide wire or catheter 900. By having the capacitance unbalanced balun unit 7000 and variable inductor 910 outside the body, the varying of the reactance (X0) of the guide wire or catheter 900 can be readily adjusted and automatically controlled by the voltage control unit circuit's reactance to the tapped voltage from the voltage-controlled oscillator in the magnetic resonance imaging unit as it is applied across X1 and X2 for any instance of time from time zero (T0) or instantiation of the magnetic resonance imaging radio-frequency pulses.

The capacitance unbalanced balun unit 7000 includes two nonmagnetic trimmer capacitors C1 and C2 connected in parallel with LC circuits (L1,C3) and (L2,C4), respectively, setting up a simplified dual T network that is effectively in series with the guide wire or catheter 900. It is noted that one end of the simplified dual T network is connected to neutral H1 and the other end is connected to a continuously variable voltage H2, based on inputs to the circuit from the voltage-controlled oscillator in the magnetic resonance imaging unit at X1 and X2. The reactance (X0) of the LC circuits in the T network is automatically adjusted to create the desired unbalanced characteristic impedance.

More specifically, the T network L1, C1, C3 and L2, C2, C4 respectively, may be used for both matching and unmatching characteristic impedance of the guide wire or catheter 900 and to provide a certain amount of balancing or unbalancing for the guide wire or catheter 900 by varying the circuit's capacitive or inductive reactance (X0).

In this example, as the voltage from the voltage-controlled oscillator in the magnetic resonance imaging unit is provided to the voltage control unit (X1 X2), the two non-magnetic trimmer capacitors C1 and C2, connected in parallel with LC circuits, (L1,C3) and (L2,C4), lift the voltage on the guide wire or catheter 900 from ground to an unbalanced state with respect to the radio-frequency pulse applied by the magnetic resonance imaging unit. The reactance of the T network and its LC circuits, (L1,C3) and (L2,C4), respectively, cause the guide wire or catheter 900 to become asymmetric and unbalanced, automatically breaking down the reactance to ensure that resonance for the guide wire or catheter 900 is never present, thus reducing the chances of thermal injury at the distal end of the guide wire or catheter 900 due to heating from induced voltages.

As noted above, a lead implanted into a biological body; e.g. a pacing lead, or a deep brain stimulation lead; is a source of potentially harmful effects to the biological body when submitted to a magnetic resonance imaging examination. These harmful effects include: 1) heating of the tissue in contact with the lead's stimulation and/or sense electrodes due to the magnetic resonance imaging scanner's so called radio frequency (or B1) field; and/or 2) improper stimulation of tissue due to induced voltages across the biological body's tissue and the lead's electrodes caused by the various changing magnetic fields produced by the magnetic resonance imaging scanner including the switched gradient fields and the radio frequency field.

To overcome or mitigate these harmful effects, various frequency dependent filters including resonant circuits (tank circuits) and/or high pass filters have been used. These circuits require the circuit components to have certain values so as to be tuned to certain frequencies.

It would be preferable to reduce or eliminate these harmful effects to the biological body by inserting non-frequency dependent circuits and/or circuit elements inline with at least some of the lead's conductors. The non-frequency dependent circuits block or reduce at least a portion of the induced currents and/or voltages in the lead or at the lead tissue interface, caused by the changing magnetic fields of the magnetic resonance imaging scanner.

The heating of tissue near a conductive electrode is essentially caused by a current passing through the tissue to or from said electrode. Since, in the simplest case, electrical power which is converted into heat is related to the second power of the current passing through a resistive material (e.g. tissue), a decrease in the current by ½ will potentially decrease the amount of harmful tissue heating by ¼.

Figure 22:
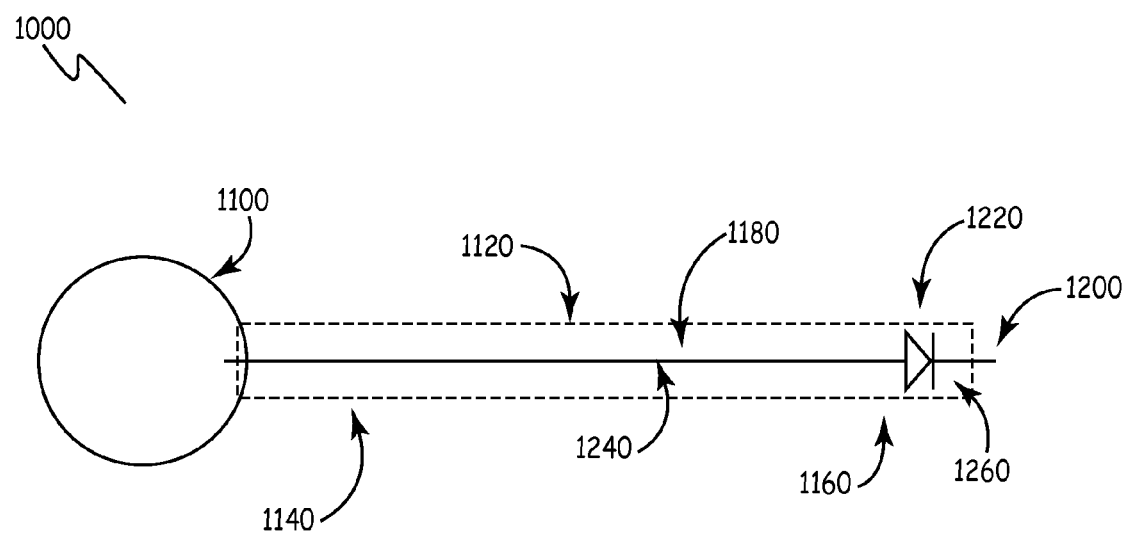
FIG. 22 illustrates an implantable therapeutic system.

FIG. 22 depicts an implantable therapeutic system 1000 including an electronics unit 1100 and a lead assembly 1120. The lead assembly 1120 has a proximal region 1140 and a distal region 1160 through which one or more conductor assemblies 1180 extends from the electronics unit 1100, through the proximal region 1140 and the distal region 1160, to end at an electrode 1200.

The electrode 1200 is in contact with biological tissue (not shown) when the therapeutic system 1000 is implanted or partially implanted into a biological body (not shown).

The conductor assembly 1180 includes a conductive wire 1240, a circuit assembly 1220, and connection 1260 to the electrode 1200. In the embodiment depicted in FIG. 22, the circuit assembly 1220 is a diode. The diode 1220 is designed such that a stimulation pulse (not shown) generated in the electronics unit 1100 can travel through the proximal region 1140, through the diode 1220 in the distal region 1160 to the electrode 1200, while significantly reducing any the magnetic resonance imaging scanner induced current from traveling from the electrode 1200 through the connector 1260 and through the diode 1220.

In one embodiment conductive wire 1240 is a multi-filar coiled wire. In another embodiment conductive wire 1240 is a single filar coiled wire. In another embodiment, conductive wire 1240 is a multi-filar braided wire.

Figure 23:
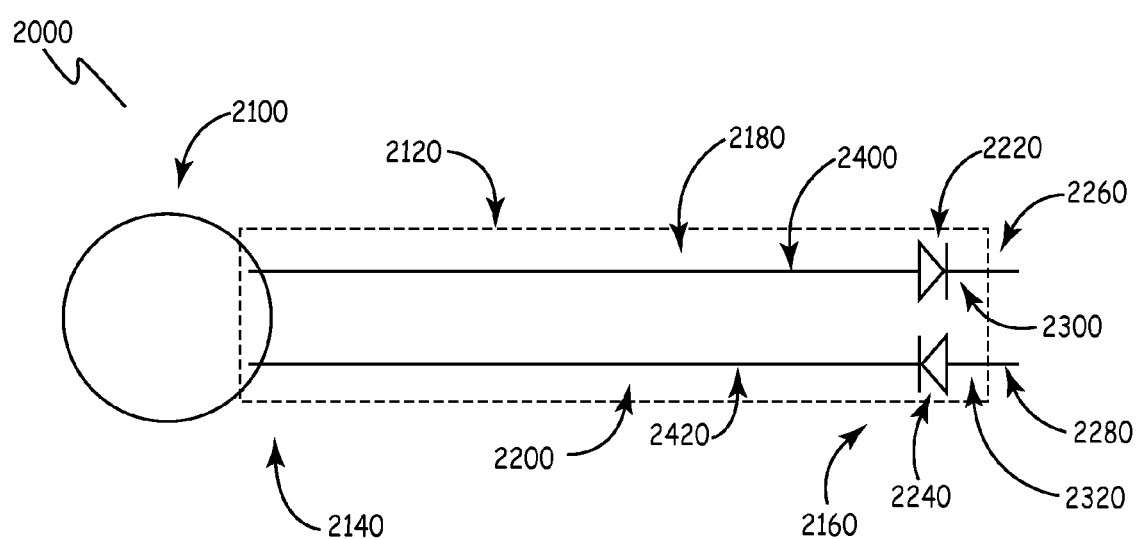
FIG. 23 illustrates a schematic of an implantable therapeutic system.

FIG. 23 is a schematic of an implantable therapeutic system 2000 including an electronics unit 2100, a lead assembly 2120 having a proximal region 2140 and a distal region 2160 such that electrodes 2260, 2280 are attached to lead assembly 2120 in the distal region 2160.

In one embodiment, the implantable therapeutic system 2000 is a bipolar pacing system. The lead assembly 2120 further includes conductor assemblies 2180 and 2200. Conductor assembly 2180 includes conductor 2400, one or more electronic elements 2220, and connection 2300 to electrode 2260. Conductor assembly 2200 includes conductor 2420, one or more electronic elements 2240, and connection 2320 to electrode 2280.

In one embodiment, electronic elements 2220 and 2240 are diodes. In the embodiment depicted in FIG. 23, the diode 2220 is designed to substantially allow a pulse, e.g. a pacing pulse or a stimulation pulse, to propagate from the electronics unit 2100 through the proximal region 2140 through conductor 2400 through diode 2220 through connection 2300 to the electrode 2260, while substantially reducing any magnetic resonance imaging induced current from traversing from the electrode 2260 through connection 2300 and through the diode 2220.

Continuing with FIG. 23, the diode 2240 is designed to substantially allow a signal; e.g. a sensing signal, to propagate to the electronics unit 2100 from the electrode 2280 through the proximal region 2240, conductor 2200, diode 2240, and connection 2320, while substantially reducing or blocking magnetic resonance imaging induced current from traveling to the electrode 2280 through connection 2320 and through the diode 2240.

Figure 24:
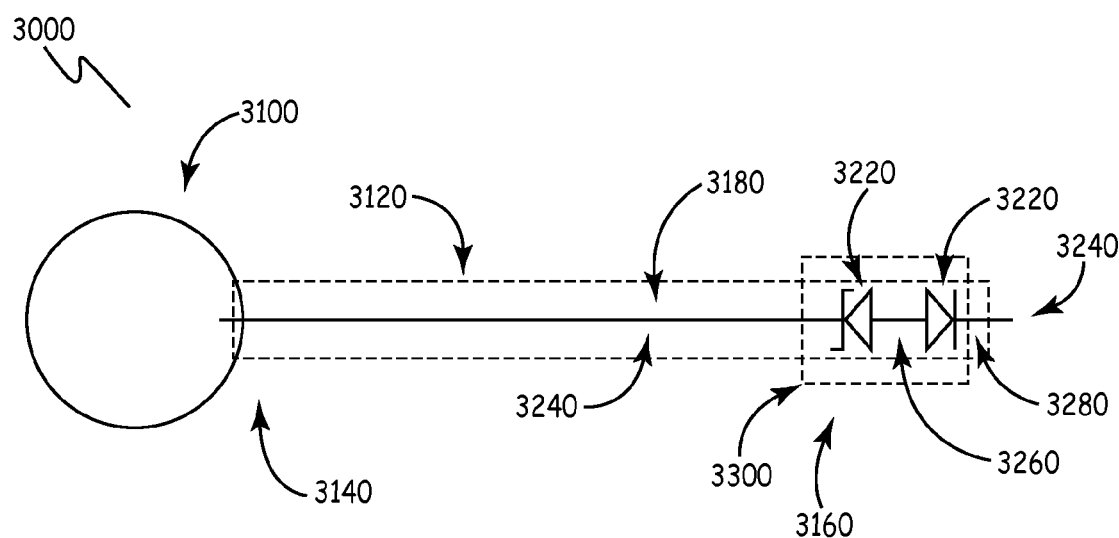
FIG. 24 illustrates another implantable therapeutic system.

FIG. 24 depicts an implantable therapeutic system 3000 including an electronics unit 3100 and a lead assembly 3120. The lead assembly 3120 has a proximal region 3140 and a distal region 3160 and through which one or more conductor assemblies 3180 extends from the electronics unit 3100 through to end at an electrode 3240. The electrode 3240 is in contact with biological tissue (not shown) when the therapeutic system 3000 is implanted or partially implanted into a biological body (not shown).

The conductor assembly 3180 includes a conductive wire 3240, a circuit assembly 3300, and connection 3280 to the electrode 3240. In the embodiment depicted in FIG. 24, the circuit assembly 3300 comprises a Zener diode 3200 and a diode 3220. The diodes 3200 and 3220 are oriented such that a stimulation pulse (not shown) generated in the electronics unit 3100 can travel through the proximal region 3140 along conductive wire 3240, through the Zener diode 3200, connection 3260, through the diode 3220, and through the connection 3280 to the electrode 3240, while significantly reducing any magnetic resonance imaging scanner induced current from traveling from the electrode 3240 through the connector 3280 and through the circuit assembly 3300.

In one embodiment, the stimulation pulse is a pacing voltage pulse. In another embodiment, the pacing pulse is greater than 4 Volts, while the reverse bias voltage (also called the backward breakdown voltage) of the Zener diode 3200 is sufficiently less than 4 volts to allow the pacing pulse to propagate through the Zener diode 3200 while blocking any other induced voltage signals that are less than 4 Volts. In one embodiment, the backward bias voltage is approximately 3 Volts.

Other types of diodes such as tunneling or Schottky diodes could be used alone or in combinations with these or other diodes or circuits to reduce the induced currents and/or voltages due to the magnetic resonance imaging scanner while not substantially altering the currents and/or voltages of the implanted or partially implanted therapeutic system.

In another embodiment, diodes are placed in series with filters, such as one or more resonant (tank) circuits, one or more notch filters, one or more high pass filters, etc. or combinations to reduce the induced currents due to the magnetic resonance imaging scanner's changing magnetic field while not significantly altering the voltages and/or currents generated by the implanted (or partially implanted) therapeutic system.

It is to be understood that the therapeutic systems depicted including an electronic unit and one or more lead assemblies are such that the lead assemblies are detachable from the electronic unit. In other embodiments, the lead assemblies are not detachable from the electronics unit. In still other embodiments, some of the lead assemblies are detachable and some are not detachable from the electronics unit.

Figure 25:
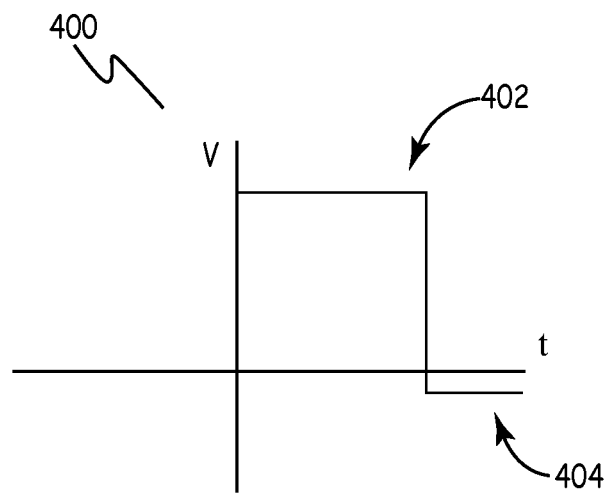
FIG. 25 is a graph of one potential type of therapeutic voltage pulse.

It is to be understood that the diode symbols used in the Figures are not necessarily indicative of the diode type to be used. That is, in some Figures, the type of diode indicated in the Figure is not the type of diode to be utilized. FIG. 25 is a graph of one potential type of therapeutic voltage pulse. In one case, this may be a pacing pulse. In this graph, the voltage pulse has a positive voltage region 402 and a negative voltage region 404. The negative region is substantially less in magnitude, but the area under the positive voltage region 402 is substantially equal to the area under the negative voltage region 404. In some situations, the negative region 404 may be longer in duration than the duration of the positive region 402.

It is to be understood that the shape of the pulse in FIG. 25 is an idealization to the actual pulse applied. That is, the actual pulse will be a more rounded shape than the sharp corners depicted. In some applications, the rise and fall times of the pulse will be significantly longer than that depicted. Additionally, the real therapeutic voltage pulse will have some small fluctuations due to environmental electromagnetic noise.

In some applications, the negative region is essentially zero voltage. In another application, the negative region fluctuates around zero voltages. In another application, the fluctuations around zero voltages are due to electromagnetic noise in the environment.

Figure 26:
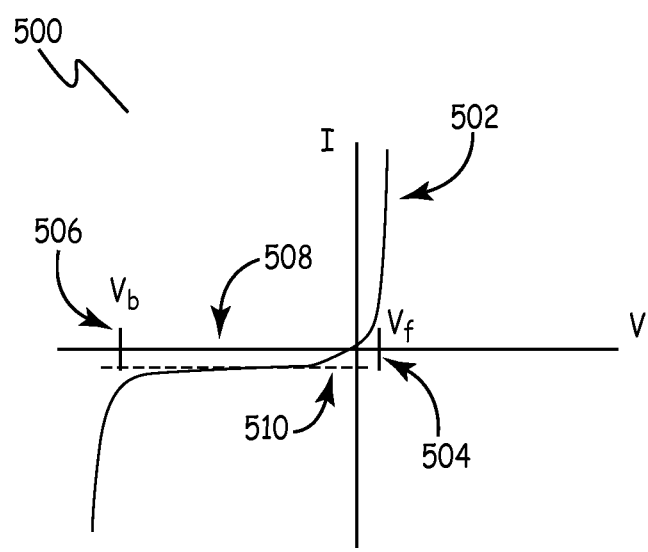
FIG. 26 is a graph of a diode's Current versus Voltage performance.

FIG. 26 is a graph 500 of a diode's Current versus Voltage performance of a Zener type diode. The diode has a forward bias voltage threshold Vf, as illustrated in FIG. 26. A voltage 504 greater than the forward bias voltage applied to the diode in the forward direction allows current to pass through the diode 502.

The diode also has a backward bias (also known as a break down) voltage (Vb in FIG. 26). A voltage greater 506 than the breakdown voltage applied in the backward direction will cause the diode to break down and allow significant current through the diode in the backward direction. Voltages less than the break down voltage applied in the backward direction will result in very little to no current 510 to flow through the diode in the backward direction.

From zero voltage to the breakdown voltage, there is a current leakage region 508 where there is the possibility of a leak current to pass through the diode in the backward direction. The magnitude of the forward bias voltage threshold Vf is less than the magnitude of the breakdown voltage Vb.

It is desirable to adjust the forward bias voltage threshold, the break down voltage threshold, and the current leakage threshold region parameters of the diode such that the therapeutic stimulation voltage pulse characteristics described in FIG. 25 can pass through the diode. That is, the breakdown voltage 506 of FIG. 26 is less than the voltage 402 of the therapeutic pulse of FIG. 25 and the leakage region 508 of FIG. 26 of the diode is sufficiently large to allow the negative voltage 404 of FIG. 25 to pass through the diode.

In another embodiment, the leakage region threshold is essentially zero volts, such that there is essentially no current flow through the diode in the backward direction for voltages applied in the backward direction until the voltage applied in the backward direction approaches the breakdown voltage threshold.

Figure 27:
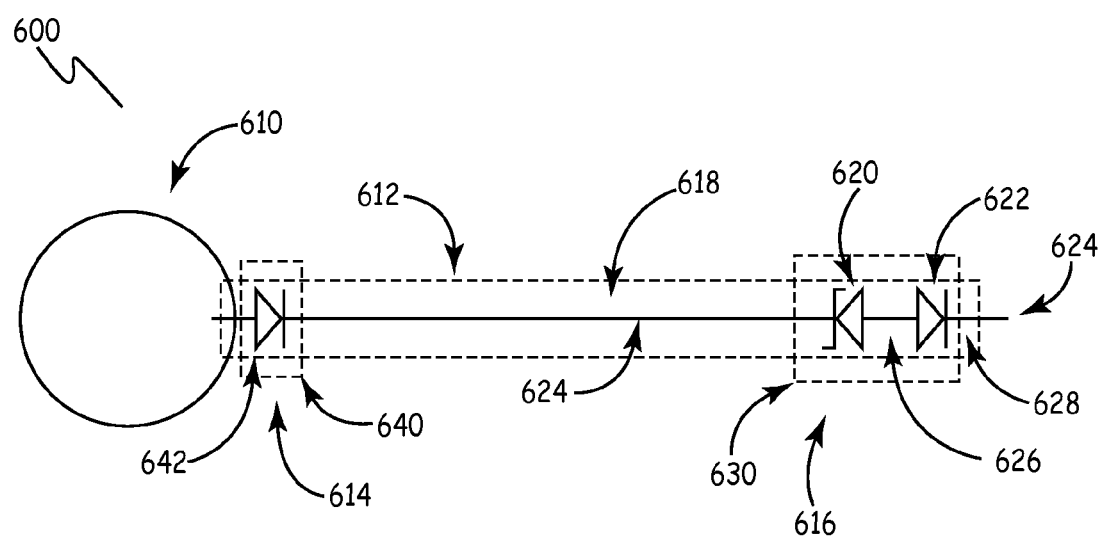
FIG. 27 illustrates another implantable therapeutic system.

FIG. 27 depicts an implantable therapeutic system 600 including an electronics unit 610 and one or more lead assemblies 612. The lead assembly 612 includes a proximal region 614 and a distal region 616. The distal region 616 includes a circuit assembly 630 including diodes 620 and 622. In one embodiment, diode 620 is a Zener diode. In one embodiment, proximal region 614 includes circuit assembly 640 including a diode 642.

In another embodiment, circuit assembly includes diodes and other circuit elements (for example, inductors, capacitors, resistors.) In other embodiments, not shown, one or more diodes are positioned along the length of the lead assembly.

Figure 28:
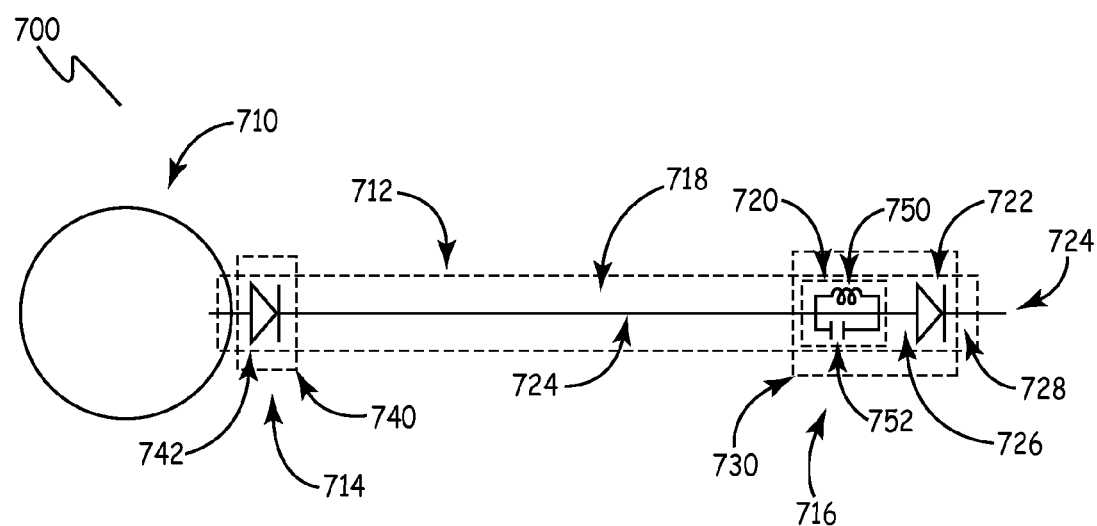
FIG. 28 illustrates another implantable therapeutic system.

FIG. 28 depicts an implantable therapeutic system 700 including an electronics unit 710 and one or more lead assemblies 712. Lead assembly 712 includes a proximal region 714 and a distal region 716. Distal region 716 includes a circuit assembly 730 which includes one of more diodes 722 and one or more circuit assemblies 720. In one embodiment, circuit assembly 720 includes at least one resonant circuit, the resonant circuit including at least one inductor 750 in parallel with at least one capacitor 752. It is to be understood that the simulations described below are for illustrative purposes only. Moreover, for comparison purposes only, the goal of each of the simulations is to produce 4 volts across the "TipTissue" interface resistor, while reducing or eliminating other so called "induced" voltages programmed into the simulations.

Figure 29:
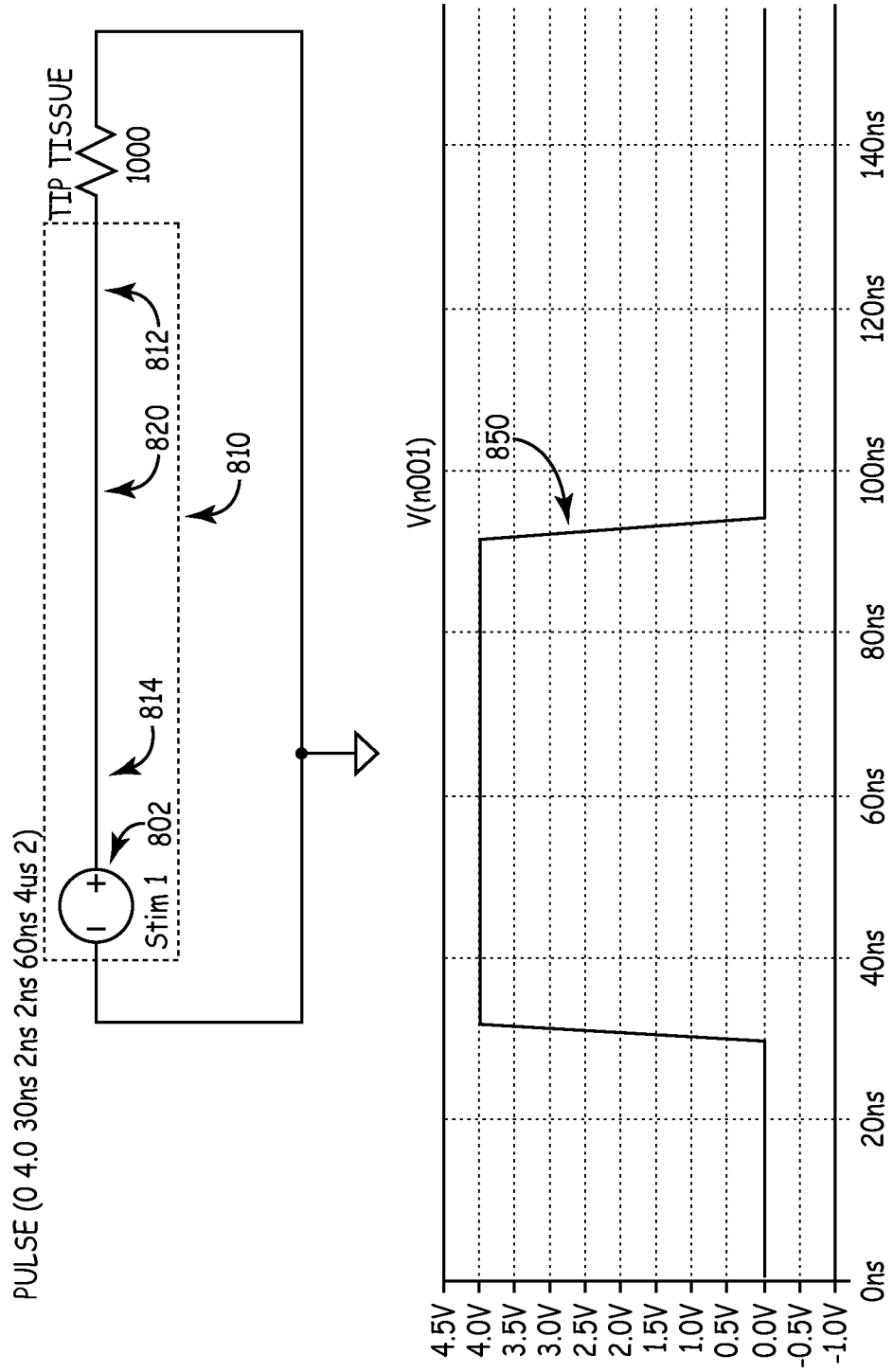
FIG. 29 illustrates a simulation of an implantable therapeutic system.

FIG. 29 depicts a simulation of an implantable therapeutic system 810 including a square wave pulse 802. The square wave pulse generator 802 produces an essentially square wave voltage pulse of 4 volts. Implantable therapeutic system 810 further includes a conductive lead 820 having a proximal region 814 near the square wave generator 802 and a distal region 812 near the "TipTissue" resistor. The "TipTissue" interface resistor represents the resistance of the tissue in contact with and adjacent to an electrode in the distal region 812 of the implantable therapeutic system.

Figure 30:
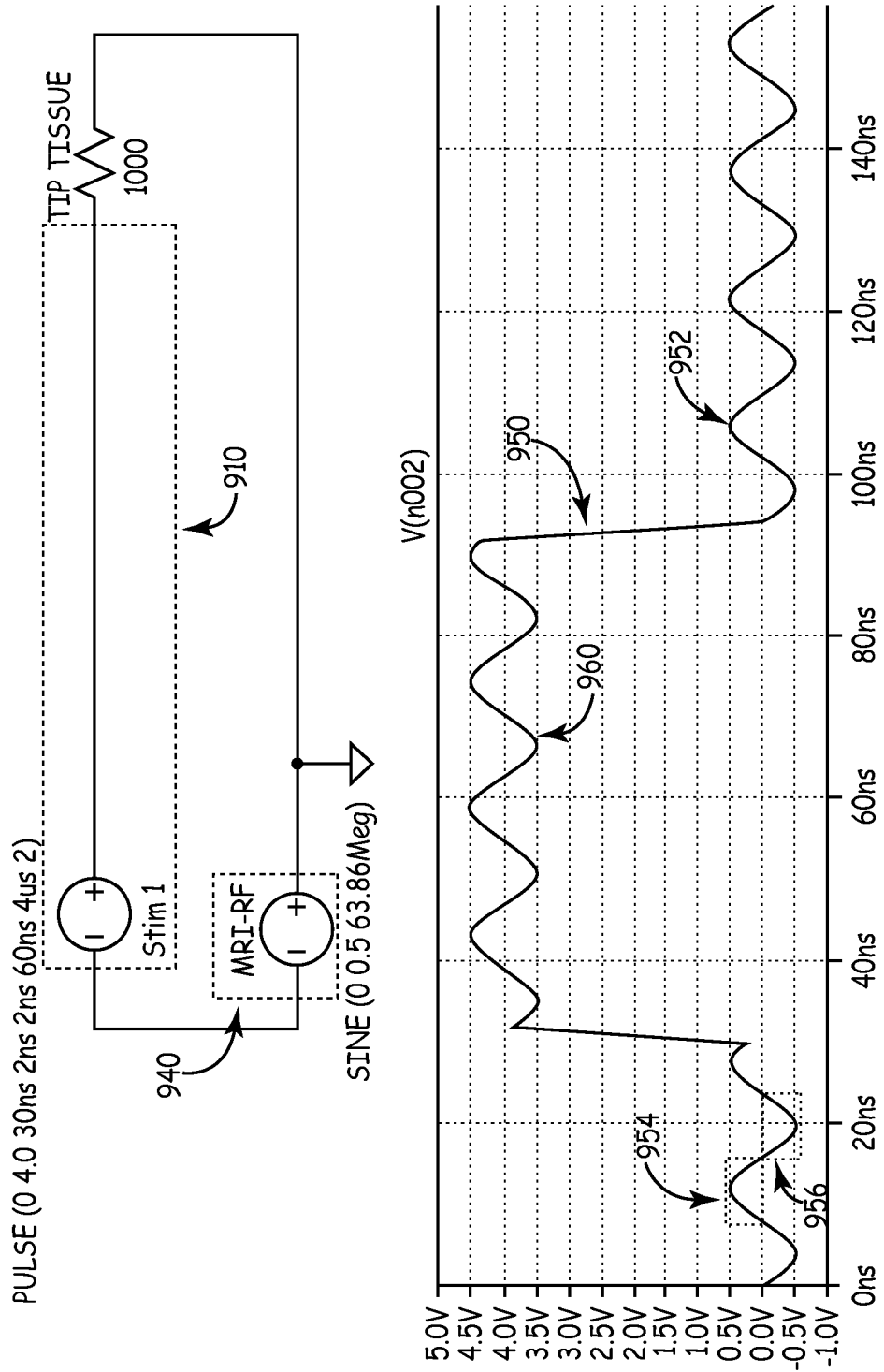
FIG. 30 illustrates another simulation of an implantable therapeutic system.

As can be seen in the graph of the voltage, across the "TipTissue" is essentially a square wave pulse 850 having amplitude of 4 volts. FIG. 30 is a simulation of an implantable therapeutic system 910. The simulation includes a tissue interface resistance "TipTisssue" 1000, a stimulation pulse generator Stim1 that provides four volt square wave pulse stimulation to the "TipTissue." Additionally, there is a sine wave voltage source 940 representing induced voltages caused by a magnetic resonance imaging scanner. The voltage from the sine wave generator 940 has amplitude of ~0.5 volts and a frequency of ~63.86 megahertz. It is to be understood that the sine wave generator is for modeling and illustrative purposes only.

The graph shows that during the application of the square wave pulse, the voltage across the "TipTissue" resistor is now a combined square wave plus an oscillating wave 950. The oscillations 960 cause the amplitude of the square wave to oscillate from 4.5 volts to 3.5 volts. At times other than during the application of the square wave pulse, there is a voltage oscillation across the "TipTissue" interface resistor 1000. The oscillating voltage has a positive value 954 and a negative value 956.

These oscillating voltages across the "TipTissue" interface resistor 1000 represent the magnetic resonance imaging induced current through the resistive tissue in contact with the electrodes of an implanted therapeutic system. Such induced currents can produce harmful thermal damage to the tissue.

Figure 31:
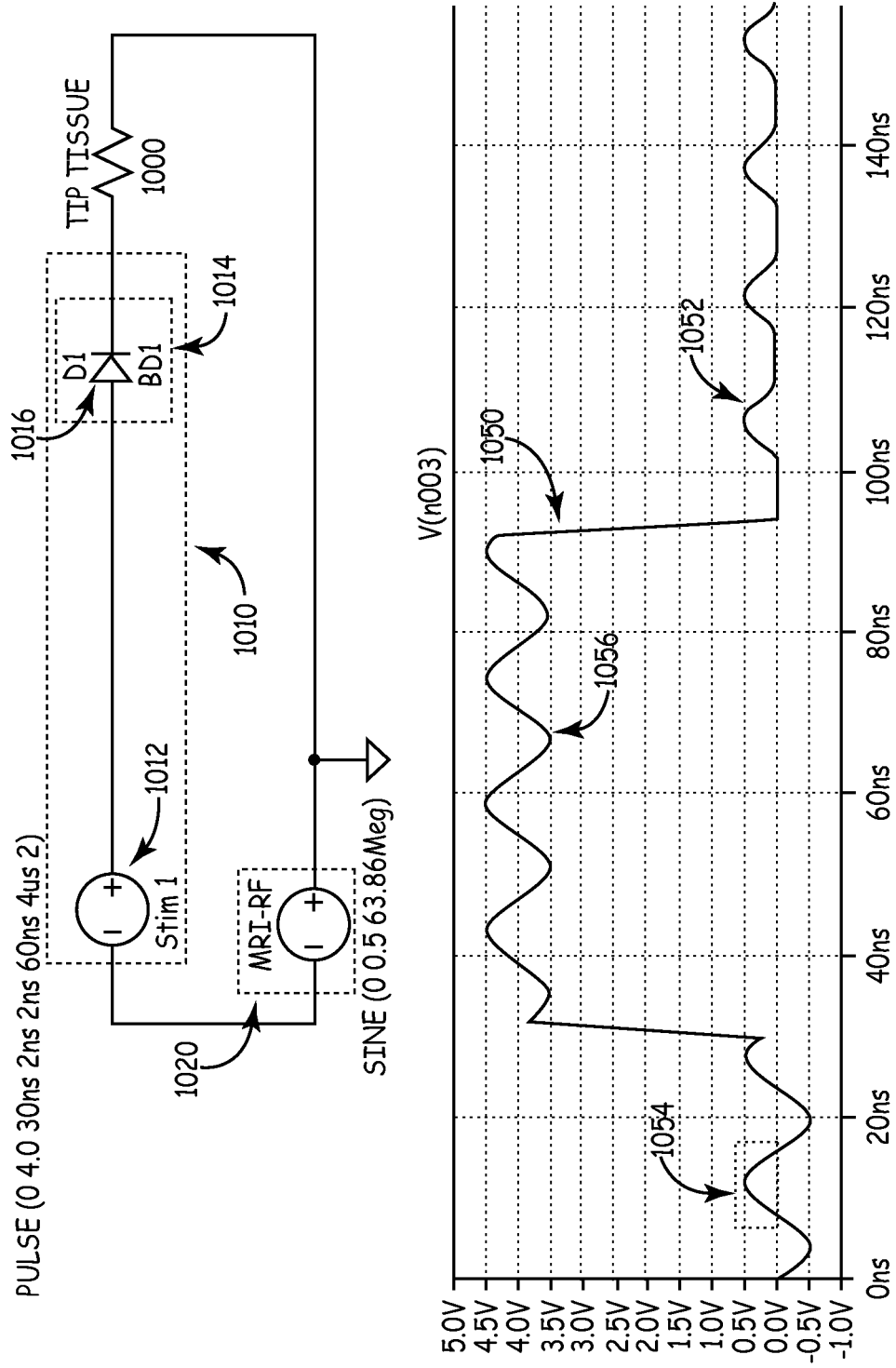
FIG. 31 illustrates another simulation of an implantable therapeutic system.

FIG. 31 depicts the simulation of an implantable therapeutic system 1010 including an electronics unit 1012 producing an essentially square wave voltage pulse of four volts and a circuit 1014 in the distal end of the therapeutic system 1010 near the "TipTissue" interface resistor 1000. The circuit 1014 includes a diode 1016. The sine wave generator 1020 produces a sine wave with amplitude of 0.5 volts at a frequency of 63.86 megahertz.

The graph in FIG. 31 depicts the voltage across the "TipTissue" interface resistor 1000. The resulting pulse 1050 has a sine wave imposed on it resulting in the amplitude of the pulse 1050 being oscillatory 1056 rather than constant.

Further, at other times before and after the square wave pulse from the electronics unit 1012, there occurs only the positive portion 1054 of the sine wave from the sine wave generator 1020. The diode 1016 blocks the negative portions of the sine wave, hence significantly reducing the heating that would occur. It is noted that the diode 1016 does not block the oscillating voltage during the square wave pulse because the square wave pulse has already turned the diode 1016 ON.

Figure 32:
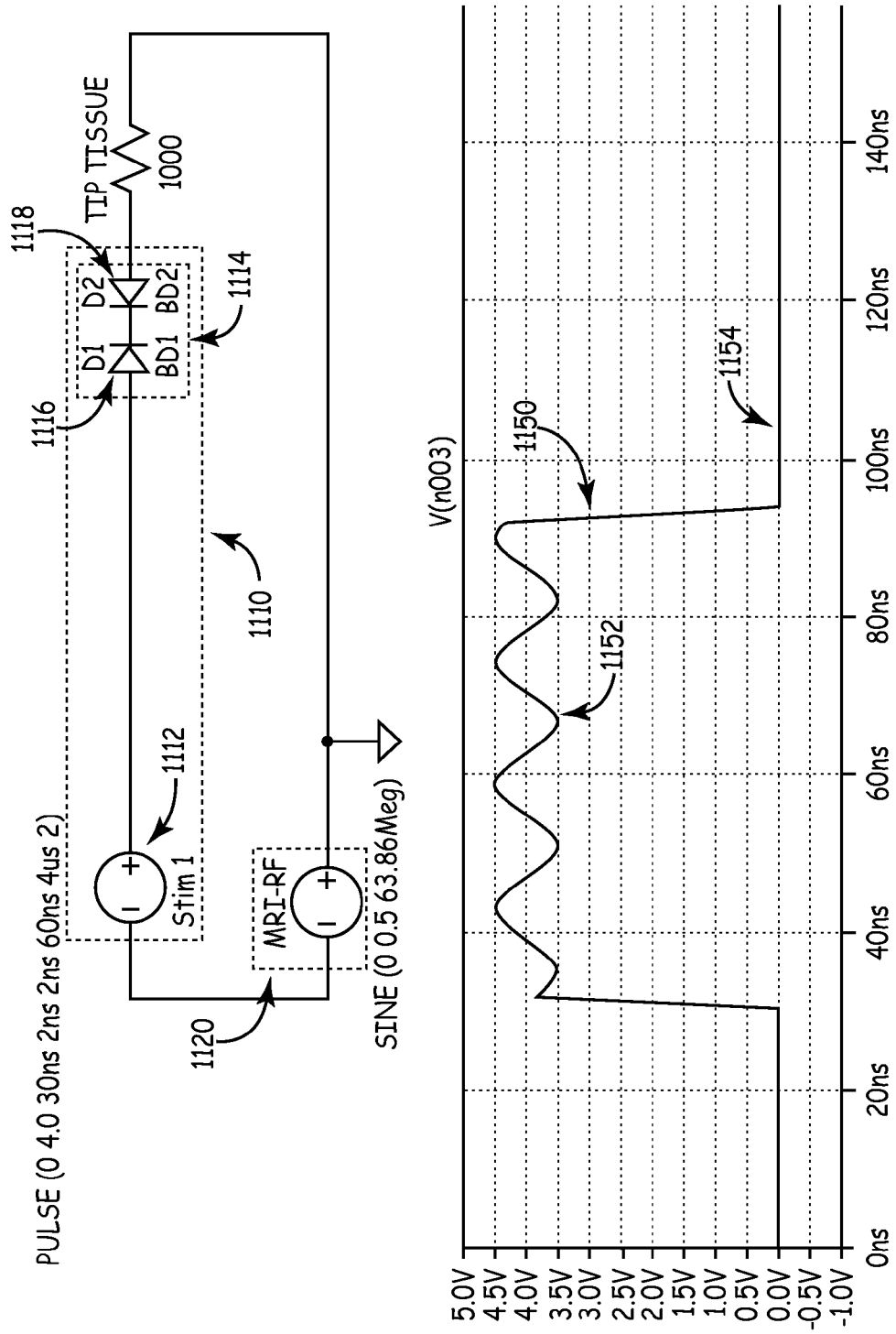
FIG. 32 illustrates another simulation of an implantable therapeutic system.

FIG. 32 depicts the simulation of an implantable therapeutic system 1110 including an electronics unit 1112 producing essentially a square wave voltage pulse of seven volts and a circuit 1114 in the distal end of the therapeutic system 1110 near the "TipTissue" interface resistor 1000. The circuit 1114 includes diodes 1116 and 1118. Diode 1118 has a backward break down voltage threshold of three volts. The sine wave generator 1120 produces a sine wave with amplitude of 0.5 volts at a frequency of 63.86 megahertz.

It is noted that the voltage of the square wave pulse from the electronics unit 1112 has been increased by the diode's 1118 break down threshold amount.

The graph of the resulting voltage 1150 across the "TipTissue" 1000 over time is again four volts from the electronics unit 1112 produced 7 volt square wave pulse plus the 0.5 sine wave 1152. At times other than during the pulse 1150, the diodes 1116 & 1118 significantly diminish the voltage 1154 across the "TipTissue" interface resistor 1000, thereby reducing any tissue heating.

Figure 33:
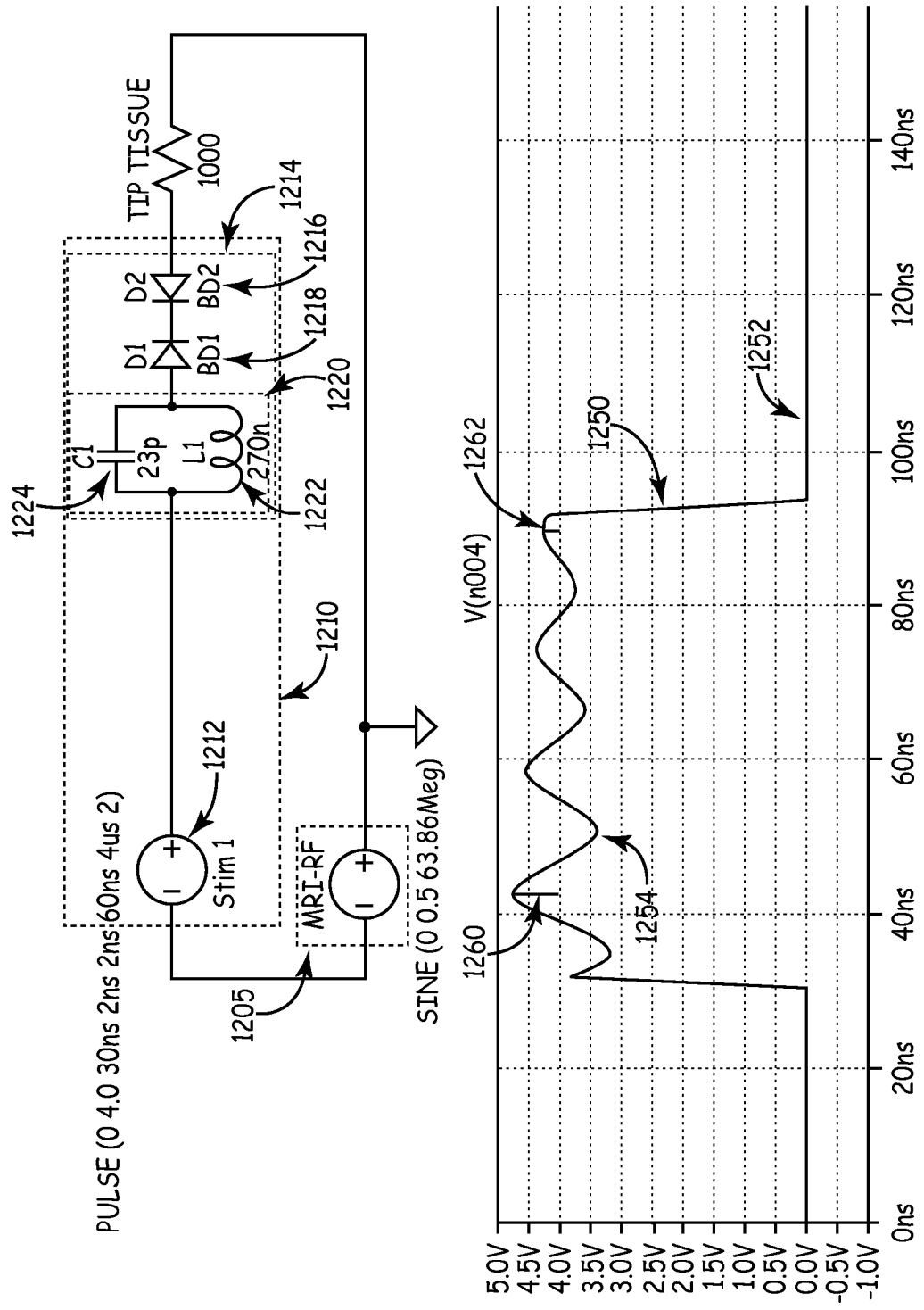
FIG. 33 illustrates another simulation of an implantable therapeutic system.

FIG. 33 depicts the simulation of an implantable therapeutic system 1210 including an electronics unit 1212 producing essentially a square wave voltage pulse of seven volts and a circuit 1214 in the distal end of the therapeutic system 1210 near the "TipTissue" interface resistor 1000. The circuit 1214 includes diodes 1216 and 1218 as well as a circuit 1220 which includes an inductor 1222 and a capacitor 1224 in parallel to form a resonant circuit 1220.

The inductor's value and the capacitor's value are chosen to make the circuit 1220 have a resonance at the frequency of the applied sign wave produced by the sine wave generator 1205. The diode 1216 has a backward break down voltage threshold of three volts. The sine wave generator 1205 produces a sine wave with amplitude of 0.5 volts at a frequency of 63.86 megahertz.

The graph of the voltage across the "TipTissue" interface resistor 1000 shows that, at times other than during the application of the square wave pulse 1250, there is negligible voltage 1252 across the interface resistor 1000.

During the square wave pulse 1250, the pulse has an oscillation 1254 due to the sine wave generator's voltage. It is seen that the amplitude of the sine wave component of the square wave pulse over time 1260 and later 1262 is diminished due to the resonant circuit 1220.

Figure 34:
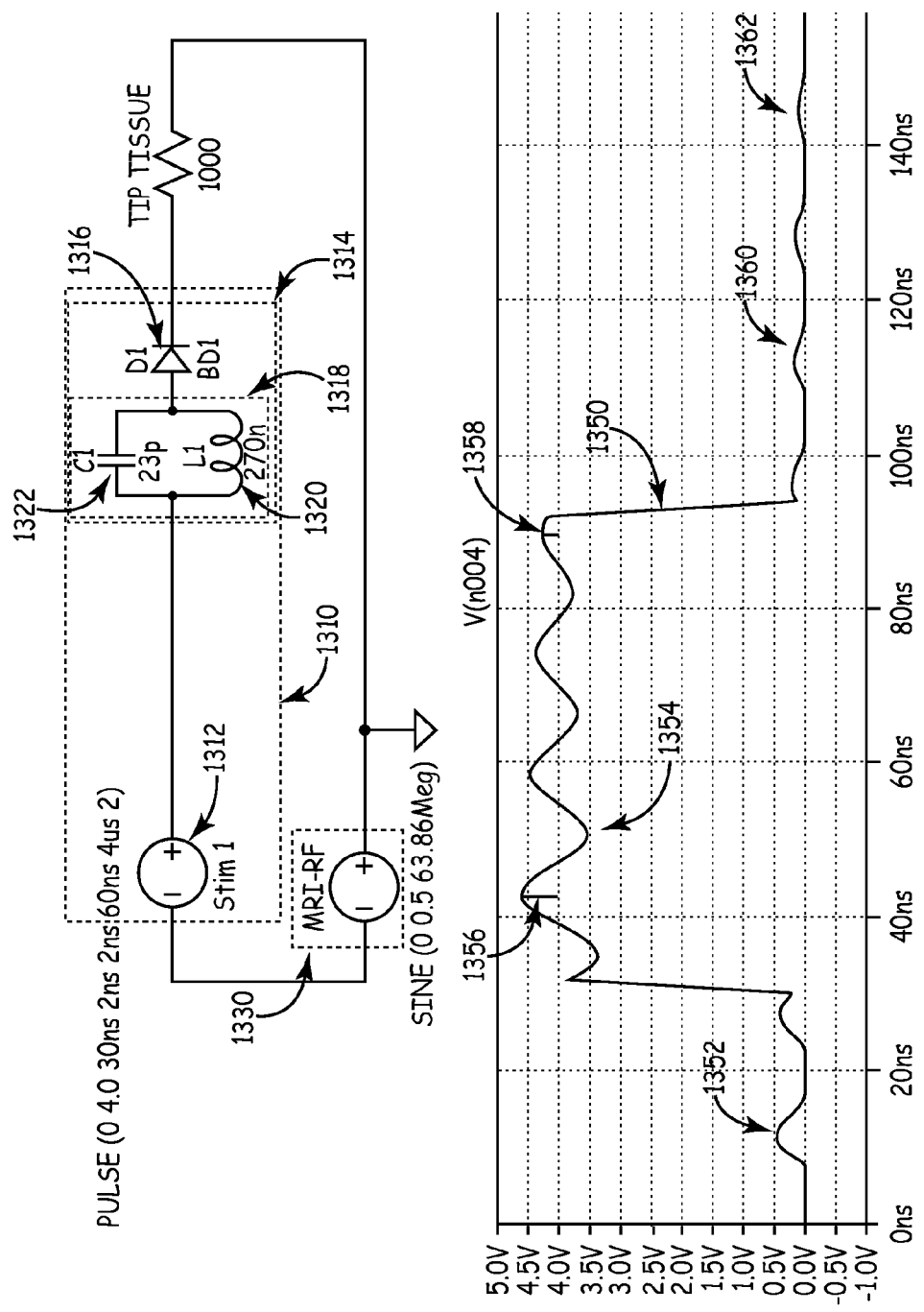
FIG. 34 illustrates another simulation of an implantable therapeutic system.

FIG. 34 depicts the simulation of an implantable therapeutic system 1310 including an electronics unit 1312 producing essentially a square wave voltage pulse of four volts and a circuit 1314 in the distal end of the therapeutic system 1310 near the "TipTissue" interface resistor 1000. The circuit 1314 includes diode 1316 as well as a circuit 1318 which includes an inductor 1320 and a capacitor 1322 in parallel to form a resonant circuit 1318.

The inductor's value and the capacitor's value are chosen to make the circuit 1318 have a resonance at the frequency of the applied sign wave produced by the sine wave generator 1330. The sine wave generator 1330 produces amplitude of 0.5 volts at a frequency of 63.86 megahertz.

It is seen from the graph of the voltage across the "TipTissue" resistor 1000 that the sine wave oscillations are diminished in amplitude 1356 & 1358 during the application of the square wave pulse 1350. At other times, the sine wave is reduced to half a sine wave 1352 by the diode 1316. Additionally, the amplitude of the half-sine wave after the square wave pulse 1350 is significantly diminished 1360 & 1362 compared to an earlier time 1352. The diminishing of the sine wave oscillations is due to the resonant circuit 1318.

Figure 35:
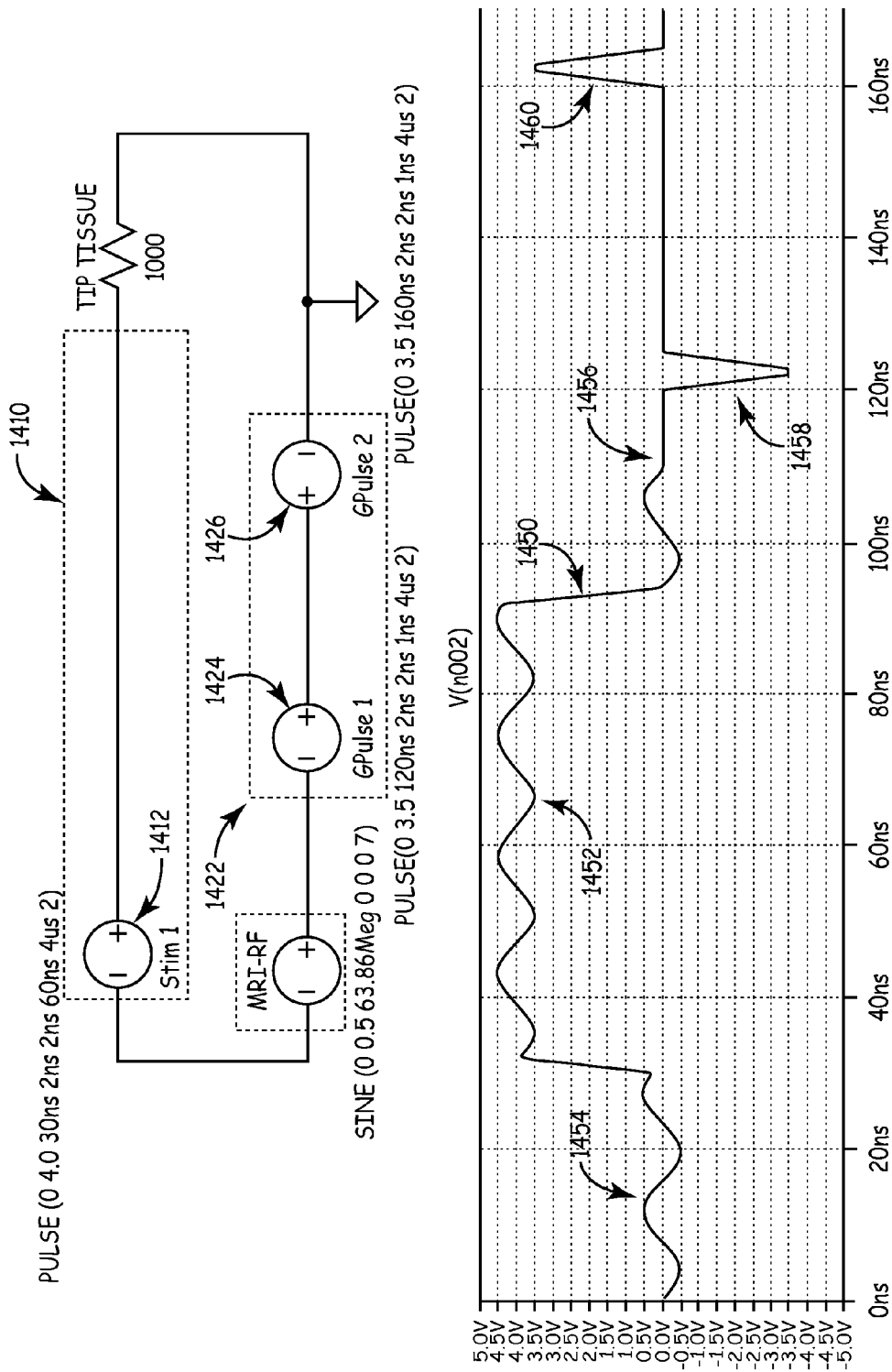
FIG. 35 illustrates another simulation of an implantable therapeutic system.

FIG. 35 depicts the simulation of an implantable therapeutic system 1410 including an electronics unit 1412 producing essentially a square wave voltage pulse of four volts. The simulation depicted further includes a sine wave generator 1420 producing a sine wave with amplitude of 0.5 volts at a frequency of 63.86 megahertz. The sine wave generator is turned OFF after a short period of time 1456.

A pulse generation system 1422 includes two pulse generators 1424 and 1426. Each of these pulse generators 1424, 1426 generates a 3.5 volt pulse. The sign of the voltage pulse from 1424 is opposite to the sign of the pulse from 1426. The two pulse generators represent, for example, a magnetic resonance imaging scanner's gradient field being turned ON and OFF.

The graph of the voltage across the "TipTissue" interface resistor 1000 shows the sine wave 1454, the square wave 1450 having an oscillating amplitude 1452, and the time 1456 at which the sign wave is turned OFF. At a later time the first gradient induce voltage 1458 is applied and still later the second gradient induced pulse 1460 is applied.

Figure 36:
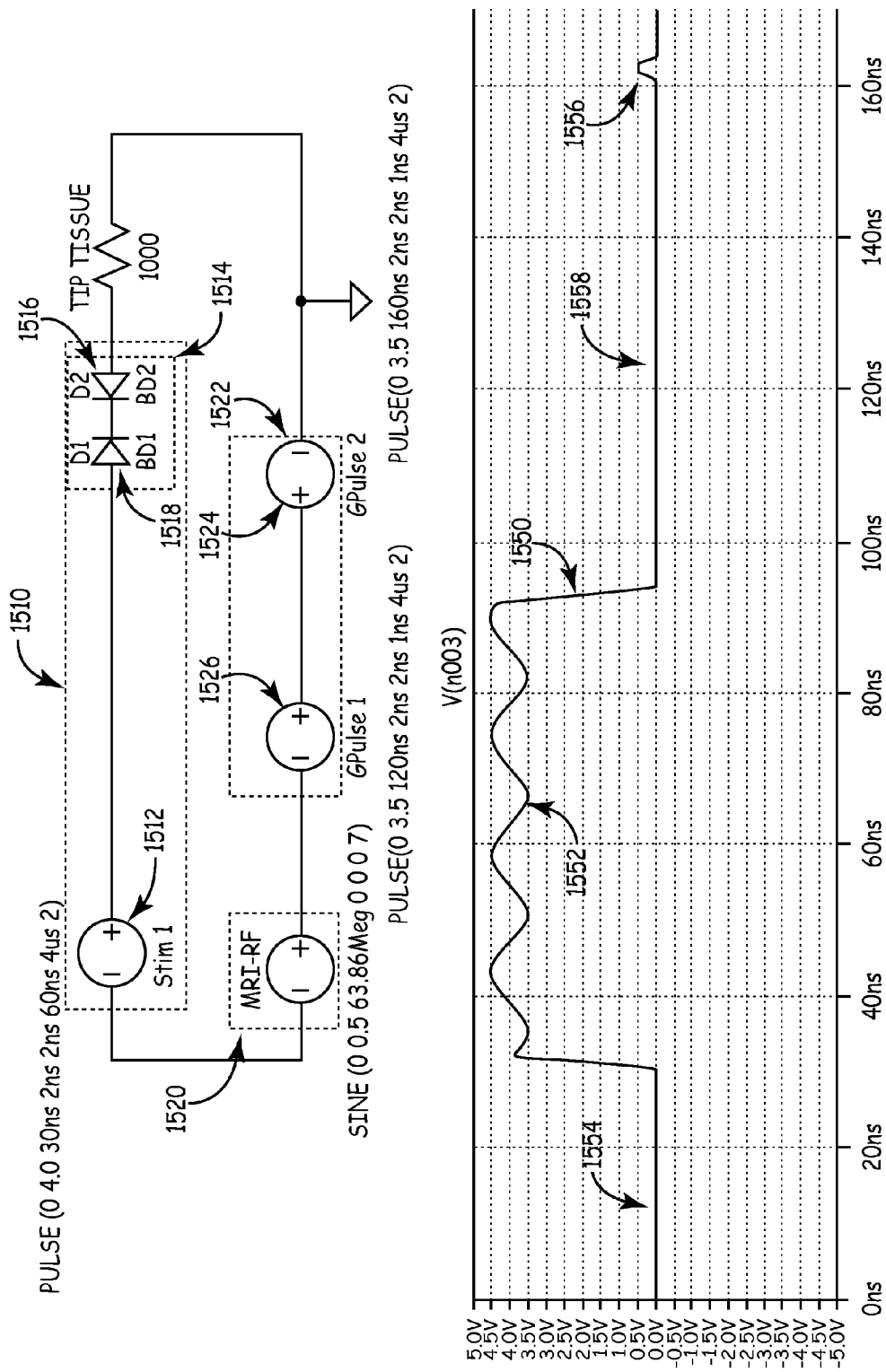
FIG. 36 illustrates another simulation of an implantable therapeutic system.

FIG. 36 depicts the simulation of an implantable therapeutic system 1510 including an electronics unit 1512 producing essentially a square wave voltage pulse of seven volts and a circuit 1514 in the distal end of the therapeutic system 1510 near the "TipTissue" interface resistor 1000. The circuit 1514 includes diodes 1516 and 1518. Diode 1516 has a backward break down voltage threshold of three volts. The sine wave generator 1520 produces a sine wave with amplitude of 0.5 volts at a frequency of 63.86 megahertz. The sine wave generator is turned OFF after the square wave pulse.

A pulse generation system 1522 includes two pulse generators 1524 and 1526. Each of these pulse generators 1524 & 1526 generates a 3.5 volt pulse. The sign of the voltage pulse from 1524 is opposite to the sign of the pulse from 1526. The two pulse generators represent, for example, a magnetic resonance imaging scanner's gradient field being turned ON and OFF.

The voltage across the "TipTissue" interface resistor 1000 is essentially that of the square wave pulse 1550 with a small oscillation 1552. At times other than during the square wave voltage pulse, the sine wave is essentially eliminated 1554 by the two diodes 1516 & 1518. The gradient induced voltage pulses at times 1558 and 1556 are also essentially eliminated. At time 1556, the gradient voltage pulse is reduced from 3.5 volts to 0.5 volts due to the break down voltage of diode 1516 being 3.0 volts.

Such reductions to the gradient induced voltages essentially eliminate any harm to the patient into which the therapeutic system has been implanted due to the gradient induced voltages.

While various examples and embodiments of the present invention have been shown and described, it will be appreciated by those skilled in the art that the spirit and scope of the present invention are not limited to the specific description and drawings herein, but extend to various modifications and changes.

What is claimed is:

1. An elongate lead assembly configured to operatively couple with an implantable medical device for delivering a therapy pulse from the implantable medical device to a patient in an environment of a changing magnetic field, the lead assembly comprising:
    a conductive wire having a proximal end proximate the implantable medical device and a distal end opposite the proximal end;
    an electrode coupled proximate the distal end of the conductive wire and configured to deliver the therapy pulse to the patient; and
    an electrical circuit operatively coupled to the conductive wire, wherein the electrical circuit is configured to:
        pass current in a first direction from the proximal end to the distal end of the conductive wire when a first voltage having a magnitude above a first voltage threshold is applied across the electrical circuit in the first direction positively biasing the electrical circuit in the first direction by the changing magnetic field; and
        pass current in a second direction opposite the first direction when a second voltage having a magnitude above a second voltage threshold is applied across the electrical circuit in the second direction by the changing magnetic field but substantially blocking current in the second direction when a voltage less than the second voltage threshold is applied across the electrical circuit in the second direction negatively biasing the electrical circuit in the first direction by the changing magnetic field.

2. A lead assembly according to claim 1 wherein the electrical circuit is a first electrical circuit and further comprising a second electrical circuit coupled in series with the electrical circuit and the first electrode, the second electrical circuit configured to substantially block current flowing in the second direction and pass current flowing in the first direction.

3. A lead assembly according to claim 2 further comprising a third electrical circuit coupled at the proximal end of the conductive wire and in series with the first and second electrical circuits, the third electrical circuit configured to substantially block current flowing in the second direction and pass current flowing in the first direction.

4. A lead assembly according to claim 1 wherein the medical device receives a sensing signal, wherein the conductive wire is a first conductive wire and the electrode is a first electrode and wherein the lead assembly further comprises:
- a second conductive wire having a proximal end proximate the implantable medical device and a distal end opposite the proximal end;
- a second electrode coupled proximate the distal end of the second conductive wire; and
- a fourth electrical circuit coupled in series with the second conductive wire and the second electrode, the fourth configured to pass the sensing pulse from the distal end to the proximal end of the second conductive wire and block a current induced from the proximal end to the distal end of the second conductive wire by the changing magnetic field.

5. The lead assembly according to claim 1 wherein the electrical circuit is configured to pass the therapy pulse from the implantable medical device to the electrode.

6. The lead assembly according to claim 1 wherein the magnitude of the first voltage threshold is less than the magnitude of the second voltage threshold.

7. The lead assembly according to claim 1 wherein the magnitude of the second voltage threshold is less than the voltage of the therapeutic pulse.

8. An elongate lead assembly configured to operatively couple with an implantable medical device for delivering a therapy pulse from the implantable medical device to a patient in an environment of a changing magnetic field, the lead assembly comprising:
- a conductive wire having a proximal end proximate the implantable medical device and a distal end opposite the proximal end;
- an electrode coupled proximate the distal end of the conductive wire and configured to deliver the therapy pulse to the patient; and
- a Zener diode operatively coupled to the conductive wire, wherein the Zener diode is configured to:
  - pass current in a first direction from the proximal end to the distal end of the conductive wire when a first voltage having a magnitude above a first voltage threshold is applied across the Zener diode in the first direction positively biasing the Zener diode in the first direction by the changing magnetic field; and
  - pass current in a second direction opposite the first direction when a second voltage having a magnitude above a second voltage threshold is applied across the Zener diode in the second direction by the changing magnetic field but substantially blocking current in the second direction when a voltage less than the second voltage threshold is applied across the Zener diode in the second direction negatively biasing the Zener diode in the first direction by the changing magnetic field.

9. A lead assembly according to claim 8, further comprising a diode coupled in series with the Zener diode and the first electrode, the diode configured to substantially block current flowing in the second direction and pass current flowing in the first direction.

10. A lead assembly according to claim 9 wherein the diode is a first diode and further comprising a second diode coupled at the proximal end of the conductive wire and in series with the Zener diode and the first diode, the second diode being configured to substantially block current flowing in the second direction and pass current flowing in the first direction.

11. The lead assembly according to claim 8 wherein the Zener diode is configured to pass the therapy pulse from the implantable medical device to the electrode.

12. The lead assembly according to claim 8 wherein the magnitude of the first voltage threshold is less than the magnitude of the second voltage threshold.

13. The lead assembly according to claim 8 wherein the magnitude of the second voltage threshold is less than the voltage of the therapeutic pulse.

* * * * *